(12) United States Patent
Juhasz et al.

(10) Patent No.: US 8,398,238 B1
(45) Date of Patent: *Mar. 19, 2013

(54) IMAGING-BASED GUIDANCE SYSTEM FOR OPHTHALMIC DOCKING USING A LOCATION-ORIENTATION ANALYSIS

(75) Inventors: Adam Juhasz, Costa Mesa, CA (US); Ilya Goldshleger, Irvine, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/218,628

(22) Filed: Aug. 26, 2011

(51) Int. Cl.
*A61B 3/14* (2006.01)
*A61B 3/10* (2006.01)
*A61B 3/00* (2006.01)

(52) U.S. Cl. .................... 351/208; 351/205; 351/246

(58) Field of Classification Search .......... 351/205–206, 351/200, 208–210, 221–223, 246
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A | 8/1985 | Ishikawa |
| 4,538,608 A | 9/1985 | L'Esperance, Jr. |
| 4,554,917 A | 11/1985 | Tagnon |
| 4,638,801 A | 1/1987 | Daly et al. |
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |

(Continued)

FOREIGN PATENT DOCUMENTS

| | | |
|---|---|---|
| EP | 1444946 | 8/2004 |
| JP | 2002345758 | 12/2002 |

(Continued)

OTHER PUBLICATIONS

PCT International Search Report and Written Opinion dated Feb. 9, 2012 for International Application Serial No. PCT/US2011/040223.

(Continued)

*Primary Examiner* — Dawayne A Pinkney

(57) ABSTRACT

An imaging-guided docking system can separate the tilt and location of an imaged ophthalmic target and present them in an intuitive manner for an ophthalmic surgeon. The docking system can include an ophthalmic imaging system to image a portion of an eye of a patient, an image processor to determine a location and an orientation of the imaged portion of the eye, and a guidance system, coupled to the ophthalmic imaging system, to guide an ophthalmic docking based on the determined location and orientation. In some implementations, the imaging system images an internal eye-structure to determine its orientation and a video-imaging system video-images a frontal eye-structure to determine a location of the frontal eye-structure. The determined orientation and location can be displayed for the surgeon. The alignment of ophthalmic procedures can also be assisted with this imaging capability, e.g. the placement and centration of IOLs into the lens capsule.

33 Claims, 20 Drawing Sheets

U.S. PATENT DOCUMENTS

| | | | |
|---|---|---|---|
| 5,139,022 | A | 8/1992 | Lempert |
| 5,246,435 | A | 9/1993 | Bille et al. |
| 5,255,025 | A | 10/1993 | Volk |
| 5,286,964 | A | 2/1994 | Fountain |
| 5,321,501 | A | 6/1994 | Swanson et al. |
| 5,336,215 | A | 8/1994 | Hsueh et al. |
| 5,391,165 | A | 2/1995 | Fountain et al. |
| 5,439,462 | A | 8/1995 | Bille et al. |
| 5,493,109 | A | 2/1996 | Wei et al. |
| 5,549,632 | A | 8/1996 | Lai |
| 5,656,186 | A | 8/1997 | Mouron et al. |
| 5,738,676 | A | 4/1998 | Hammer et al. |
| 5,779,696 | A | 7/1998 | Berry et al. |
| 5,795,295 | A | 8/1998 | Hellmuth et al. |
| 5,936,706 | A | 8/1999 | Takagi |
| 5,954,648 | A | 9/1999 | Van Der Brug |
| 5,954,711 | A | 9/1999 | Ozaki et al. |
| 5,994,690 | A | 11/1999 | Kulkarni et al. |
| 6,004,314 | A | 12/1999 | Wei et al. |
| 6,095,648 | A | 8/2000 | Birngruber et al. |
| 6,099,522 | A | 8/2000 | Knopp et al. |
| 6,137,585 | A | 10/2000 | Hitzenberger et al. |
| 6,254,595 | B1 | 7/2001 | Juhasz et al. |
| 6,288,784 | B1 | 9/2001 | Hitzenberger et al. |
| 6,314,311 | B1 | 11/2001 | Williams et al. |
| 6,317,616 | B1 | 11/2001 | Glossop |
| 6,337,925 | B1 | 1/2002 | Cohen et al. |
| 6,377,349 | B1 | 4/2002 | Fercher |
| 6,379,005 | B1 | 4/2002 | Williams et al. |
| 6,451,009 | B1 | 9/2002 | Dasilva et al. |
| 6,454,761 | B1 | 9/2002 | Freedman |
| 6,497,701 | B2 | 12/2002 | Shimmick et al. |
| 6,529,758 | B2 | 3/2003 | Shahidi |
| 6,579,282 | B2 | 6/2003 | Bille et al. |
| 6,623,476 | B2 | 9/2003 | Juhasz et al. |
| 6,687,010 | B1 | 2/2004 | Horii et al. |
| 6,730,074 | B2 | 5/2004 | Bille et al. |
| 6,741,359 | B2 | 5/2004 | Wei et al. |
| 6,751,033 | B2 | 6/2004 | Goldstein et al. |
| 6,755,819 | B1 | 6/2004 | Waelti |
| 6,763,259 | B1 | 7/2004 | Hauger et al. |
| 6,769,769 | B2 | 8/2004 | Podoleanu et al. |
| 6,775,007 | B2 | 8/2004 | Izatt et al. |
| 6,863,667 | B2 | 3/2005 | Webb et al. |
| 6,887,232 | B2 | 5/2005 | Bille |
| 6,899,707 | B2 | 5/2005 | Scholler et al. |
| 6,932,807 | B1 | 8/2005 | Tomita et al. |
| 6,991,629 | B1 | 1/2006 | Juhasz et al. |
| 7,006,232 | B2 | 2/2006 | Rollins et al. |
| 7,018,376 | B2 | 3/2006 | Webb et al. |
| 7,027,233 | B2 | 4/2006 | Goldstein et al. |
| 7,061,622 | B2 | 6/2006 | Rollins et al. |
| 7,072,045 | B2 | 7/2006 | Chen et al. |
| 7,072,047 | B2 | 7/2006 | Westphal et al. |
| 7,079,254 | B2 | 7/2006 | Kane et al. |
| 7,102,756 | B2 | 9/2006 | Izatt et al. |
| 7,113,818 | B2 | 9/2006 | Podoleanu et al. |
| 7,126,693 | B2 | 10/2006 | Everett et al. |
| 7,130,054 | B2 | 10/2006 | Ostrovsky et al. |
| 7,133,137 | B2 | 11/2006 | Shimmick |
| 7,139,077 | B2 | 11/2006 | Podoleanu et al. |
| 7,145,661 | B2 | 12/2006 | Hitzenberger |
| 7,148,970 | B2 | 12/2006 | de Boer |
| 7,184,148 | B2 | 2/2007 | Alphonse |
| 7,207,983 | B2 | 4/2007 | Hahn et al. |
| 7,248,371 | B2 | 7/2007 | Chan et al. |
| 7,268,885 | B2 | 9/2007 | Chan et al. |
| 7,280,221 | B2 | 10/2007 | Wei |
| 7,307,733 | B2 | 12/2007 | Chan et al. |
| 7,310,150 | B2 | 12/2007 | Guillermo et al. |
| 7,312,876 | B2 | 12/2007 | Chan et al. |
| 7,319,566 | B2 | 1/2008 | Prince et al. |
| 7,329,002 | B2 | 2/2008 | Nakanishi |
| 7,330,270 | B2 | 2/2008 | O'Hara et al. |
| 7,330,273 | B2 | 2/2008 | Podoleanu et al. |
| 7,335,223 | B2 | 2/2008 | Obrebski |
| 7,336,366 | B2 | 2/2008 | Choma et al. |
| 7,342,659 | B2 | 3/2008 | Horn et al. |
| 7,347,548 | B2 | 3/2008 | Huang et al. |
| 7,352,444 | B1 | 4/2008 | Seams et al. |
| 7,355,716 | B2 | 4/2008 | de Boer et al. |
| 7,364,296 | B2 | 4/2008 | Miller et al. |
| 7,365,856 | B2 | 4/2008 | Everett et al. |
| 7,365,859 | B2 | 4/2008 | Yun et al. |
| 7,370,966 | B2 | 5/2008 | Fukuma et al. |
| 7,371,230 | B2 | 5/2008 | Webb et al. |
| 7,372,578 | B2 | 5/2008 | Akiba et al. |
| 7,388,672 | B2 | 6/2008 | Zhou et al. |
| 7,390,089 | B2 | 6/2008 | Loesel et al. |
| 7,400,410 | B2 | 7/2008 | Baker et al. |
| 7,402,159 | B2 | 7/2008 | Loesel et al. |
| 7,426,037 | B2 | 9/2008 | Ostrovsky et al. |
| 7,433,046 | B2 | 10/2008 | Everett et al. |
| 7,452,077 | B2 | 11/2008 | Meyer et al. |
| 7,461,658 | B2 | 12/2008 | Jones et al. |
| 7,466,423 | B2 | 12/2008 | Podoleanu et al. |
| 7,477,764 | B2 | 1/2009 | Haisch |
| 7,480,058 | B2 | 1/2009 | Zhao et al. |
| 7,480,059 | B2 | 1/2009 | Zhou et al. |
| 7,488,070 | B2 | 2/2009 | Hauger et al. |
| 7,488,930 | B2 | 2/2009 | Ajgaonkar et al. |
| 7,492,466 | B2 | 2/2009 | Chan et al. |
| 7,503,916 | B2 | 3/2009 | Shimmick |
| 7,508,525 | B2 | 3/2009 | Zhou et al. |
| 7,535,577 | B2 | 5/2009 | Podoleanu et al. |
| 7,537,591 | B2 | 5/2009 | Feige et al. |
| 7,557,928 | B2 | 7/2009 | Ueno |
| 7,575,322 | B2 | 8/2009 | Somani |
| 7,593,559 | B2 | 9/2009 | Toth et al. |
| 7,602,500 | B2 | 10/2009 | Izatt et al. |
| 7,604,351 | B2 | 10/2009 | Fukuma et al. |
| 7,614,744 | B2 | 11/2009 | Abe |
| 7,630,083 | B2 | 12/2009 | de Boer et al. |
| 7,631,970 | B2 | 12/2009 | Wei |
| 7,633,627 | B2 | 12/2009 | Choma et al. |
| 7,643,152 | B2 | 1/2010 | de Boer et al. |
| 7,813,644 | B2 | 10/2010 | Chen et al. |
| 7,898,712 | B2 | 3/2011 | Adams et al. |
| 2001/0022648 | A1 | 9/2001 | Lai |
| 2002/0013574 | A1 | 1/2002 | Elbrecht et al. |
| 2002/0082466 | A1 | 6/2002 | Han |
| 2002/0097374 | A1 | 7/2002 | Payne et al. |
| 2002/0133145 | A1 | 9/2002 | Gerlach et al. |
| 2002/0198516 | A1 | 12/2002 | Knopp |
| 2003/0090674 | A1 | 5/2003 | Zeylikovich et al. |
| 2003/0206272 | A1 | 11/2003 | Cornsweet et al. |
| 2004/0039378 | A1 | 2/2004 | Lin |
| 2004/0059321 | A1 | 3/2004 | Knopp et al. |
| 2004/0151466 | A1 | 8/2004 | Crossman-Bosworth et al. |
| 2004/0243233 | A1 | 12/2004 | Phillips |
| 2005/0010109 | A1 | 1/2005 | Faul |
| 2005/0015120 | A1 | 1/2005 | Seibel et al. |
| 2005/0021011 | A1 | 1/2005 | LaHaye |
| 2005/0173817 | A1 | 8/2005 | Fauver et al. |
| 2005/0192562 | A1 | 9/2005 | Loesel et al. |
| 2005/0201633 | A1 | 9/2005 | Moon et al. |
| 2005/0203492 | A1 | 9/2005 | Nguyen et al. |
| 2005/0215986 | A1 | 9/2005 | Chernyak et al. |
| 2005/0284774 | A1 | 12/2005 | Mordaunt |
| 2005/0286019 | A1 | 12/2005 | Wiltberger et al. |
| 2005/0288745 | A1 | 12/2005 | Andersen et al. |
| 2006/0020172 | A1 | 1/2006 | Luerssen et al. |
| 2006/0077346 | A1 | 4/2006 | Matsumoto |
| 2006/0100613 | A1 | 5/2006 | McArdle et al. |
| 2006/0179992 | A1 | 8/2006 | Kermani |
| 2006/0187462 | A1 | 8/2006 | Srinivasan et al. |
| 2006/0195076 | A1* | 8/2006 | Blumenkranz et al. ........... 606/4 |
| 2006/0206102 | A1 | 9/2006 | Shimmick |
| 2007/0013867 | A1 | 1/2007 | Ichikawa |
| 2007/0121069 | A1 | 5/2007 | Andersen et al. |
| 2007/0126985 | A1 | 6/2007 | Wiltberger et al. |
| 2007/0129709 | A1 | 6/2007 | Andersen et al. |
| 2007/0129775 | A1 | 6/2007 | Mordaunt et al. |
| 2007/0147730 | A1 | 6/2007 | Wiltberger et al. |
| 2007/0173791 | A1 | 7/2007 | Raksi |
| 2007/0173794 | A1 | 7/2007 | Frey et al. |
| 2007/0173795 | A1 | 7/2007 | Frey et al. |

| | | |
|---|---|---|
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0282313 A1 | 12/2007 | Huang et al. |
| 2007/0291277 A1 | 12/2007 | Everett et al. |
| 2007/0299429 A1 | 12/2007 | Amano |
| 2008/0033406 A1 | 2/2008 | Andersen et al. |
| 2008/0049188 A1 | 2/2008 | Wiltberger et al. |
| 2008/0055543 A1 | 3/2008 | Meyer et al. |
| 2008/0056610 A1 | 3/2008 | Kanda |
| 2008/0071254 A1 | 3/2008 | Lummis et al. |
| 2008/0088795 A1 | 4/2008 | Goldstein et al. |
| 2008/0100612 A1 | 5/2008 | Dastmalchi et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0088734 A1 | 4/2009 | Mordaunt |
| 2009/0125005 A1 | 5/2009 | Chernyak et al. |
| 2009/0131921 A1 | 5/2009 | Kurtz et al. |
| 2009/0149742 A1 | 6/2009 | Kato et al. |
| 2009/0157062 A1 | 6/2009 | Hauger et al. |
| 2009/0161827 A1* | 6/2009 | Gertner et al. ............... 378/65 |
| 2009/0168017 A1 | 7/2009 | O'Hara et al. |
| 2009/0268161 A1 | 10/2009 | Hart et al. |
| 2010/0004641 A1 | 1/2010 | Frey et al. |
| 2010/0004643 A1 | 1/2010 | Frey et al. |
| 2010/0007848 A1 | 1/2010 | Murata |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |
| 2010/0324543 A1 | 12/2010 | Kurtz et al. |
| 2011/0022036 A1 | 1/2011 | Frey et al. |
| 2011/0118609 A1* | 5/2011 | Goldshleger et al. ......... 600/476 |
| 2011/0319873 A1* | 12/2011 | Raksi et al. ....................... 606/1 |

FOREIGN PATENT DOCUMENTS

| | | |
|---|---|---|
| WO | 98/08048 | 2/1998 |
| WO | 2006074469 | 7/2006 |
| WO | 2007106326 | 9/2007 |
| WO | 2007/130411 | 11/2007 |

OTHER PUBLICATIONS

Arimoto et al., "Imaging Properties of Axicon in a Scanning Optical System," Nov. 1, 1992, Applied Optics, 31 (31):6652-6657.

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27.

Chinn, S.R., et al., "Optical coherence tomography using a frequency-tunable optical source", Optics Letters, 22 (5):340-342, Mar. 1997.

European Search Report, European Patent Application No. 10191057.8, mailed Mar. 16, 2011, to be published by the USPTO.

Fercher et al., "Eye-Length Measurement by Interferometry With Partially Coherent Light," Mar. 1988, Optics Letters, 13(3):186-188.

Fercher et al., "Measurement of Intraocular Distances by Backscattering Spectral Interferometry," May 15, 1995, Optics Comm. 117:43-48.

Hee, M., et al., "Femtosecond transillumination optical coherence tomography", Optics Letters, 18(12):950-952, Jun. 1993.

Huber, R., et al., "Three-dimensional and C-mode OCT imaging with a compact, frequency swept laser source at 1300 nm", Optics Express, 13(26):10523-10538, Dec. 2005.

Izatt et al., "Micron-Resolution Biomedical Imaging With Optical Coherence Tomography," Oct. 1993, Optics & Photonics News, pp. 14-19.

Kamensky, V., et al., "In situ monitoring of the middle IR laser ablation of a cataract-suffered human lens by optical coherent tomography", Proc. SPIE, 2930:222-229, 1996.

Kamensky, V., et al., "Monitoring and animation of laser ablation process in cataracted eye lens using coherence tomography", Proc. SPIE, 2981:94-102, 1997.

Massow, O., et al., "Optical coherence tomography controlled femtosecond laser microsurgery system", Proceedings of the SPIE—Optical Coherence Tomography and Coherence Techniques III, vol. 6627, pp. 662717(1)-662717(6), Aug. 2007.

Ohmi, M., et al., "In-situ Observation of Tissue Laser Ablation Using Optical Coherence Tomography", Optical and Quantum Electronics, 37(13-15):1175-1183, Dec. 2005.

Ostaszewski et al., "Risley prism Beam Pointer", Proc. of SPIE, vol. 6304, 630406-1 thru 630406-10.

PCT International Search Report for International Application No. PCT/US2011/023710 mailed Aug. 24, 2011.

PCT International Search Report for International Application No. PCT/US2011/025332 mailed Sep. 16, 2011.

PCT International Search Report for International Application No. PCT/US2010/056701 mailed Jan. 12, 2011.

PCT International Search Report for International Application No. PCT/US2008/075511 mailed Mar. 12, 2009.

Sarunic, M. et al. "Instantaneous complex conjugate resolved spectral domain and swept-source OCT using 3×3 fiber couplers", Optics Express, 13(3):957-967, Feb. 2005.

Sarunic, M., et al., "Real-time quadrature projection complex conjugate resolved Fourier domain optical coherence tomography", Optics Letters, 31(16):2426-2428, Aug. 2006.

Sarunic, M., et al., "Imaging the Ocular Anterior Segment With Real-Time, Full-Range Fourier-Domain Optical Coherence Tomography", Archives of Ophthalmology, 126(4):537-542, Apr. 2008.

Stern et al., "Femtosecond Optical Ranging of Corneal Incision Depth," Jan. 1989, Investigative Ophthalmology & Visual Science, 30(1):99-104.

Swanson et al., "In vivo retinal imaging by optical coherence tomography", Optics Letters, 18(21), 1864-1866, Nov. 1993.

Tao, Y., et al., "High-speed complex conjugate resolved retinal spectral domain optical coherence tomography using sinusoidal phase modulation", Optics letters, 32(20):2918-2920, Oct. 2007.

Wojtkowski et al., "In Vivo Human Retinal Imaging by Fourier Domain Optical Coherence Tomography," Jul. 2002, Journal of Biomedical Optics 7(3):457-463, 7 pages.

Yun, S.H., et al., "Wavelength-swept fiber laser with frequency shifted feedback and resonantly swept intra-cavity acoustooptic tunable filter", IEEE Journal of Selected Topics in Quantum Electronics, 3(4):1087-1096, Aug. 1997.

PCT International Search Report corresponding to PCT Application Serial No. PCT/US2011/051466 dated Apr. 10, 2012.

Partial International Search Report corresponding to PCT Application Serial No. PCT/US2012/035927 dated Aug. 3, 2012.

* cited by examiner

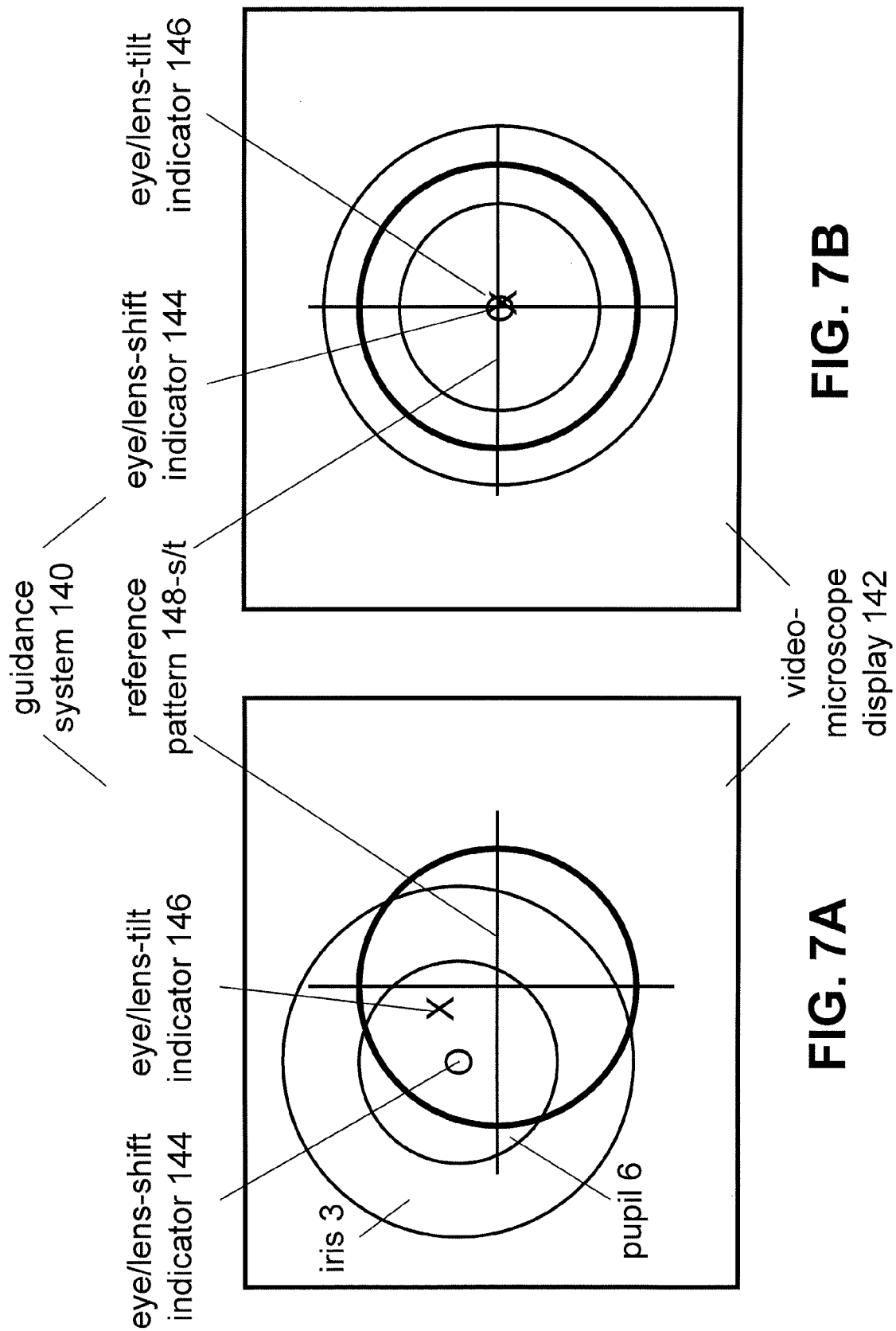

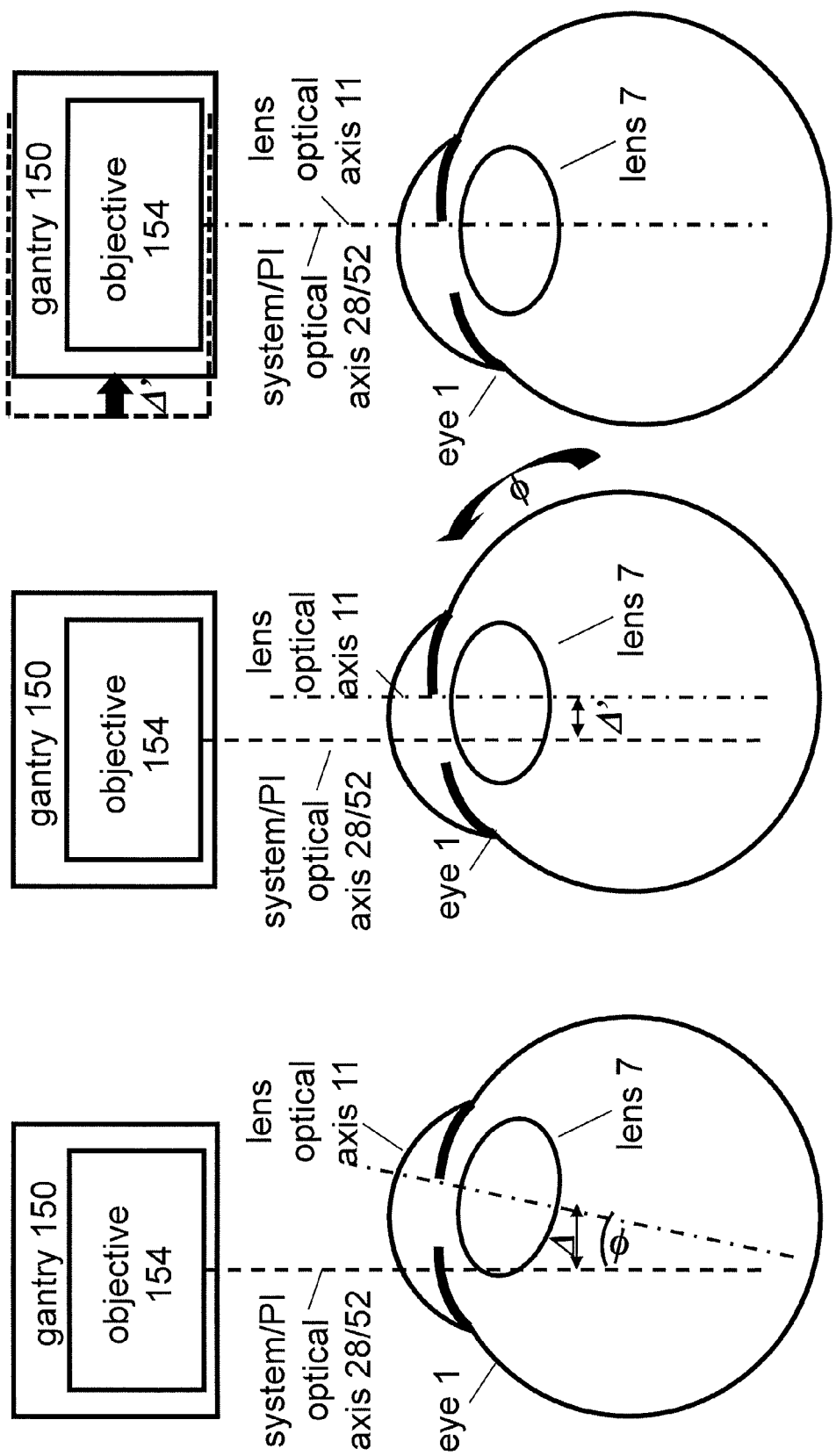

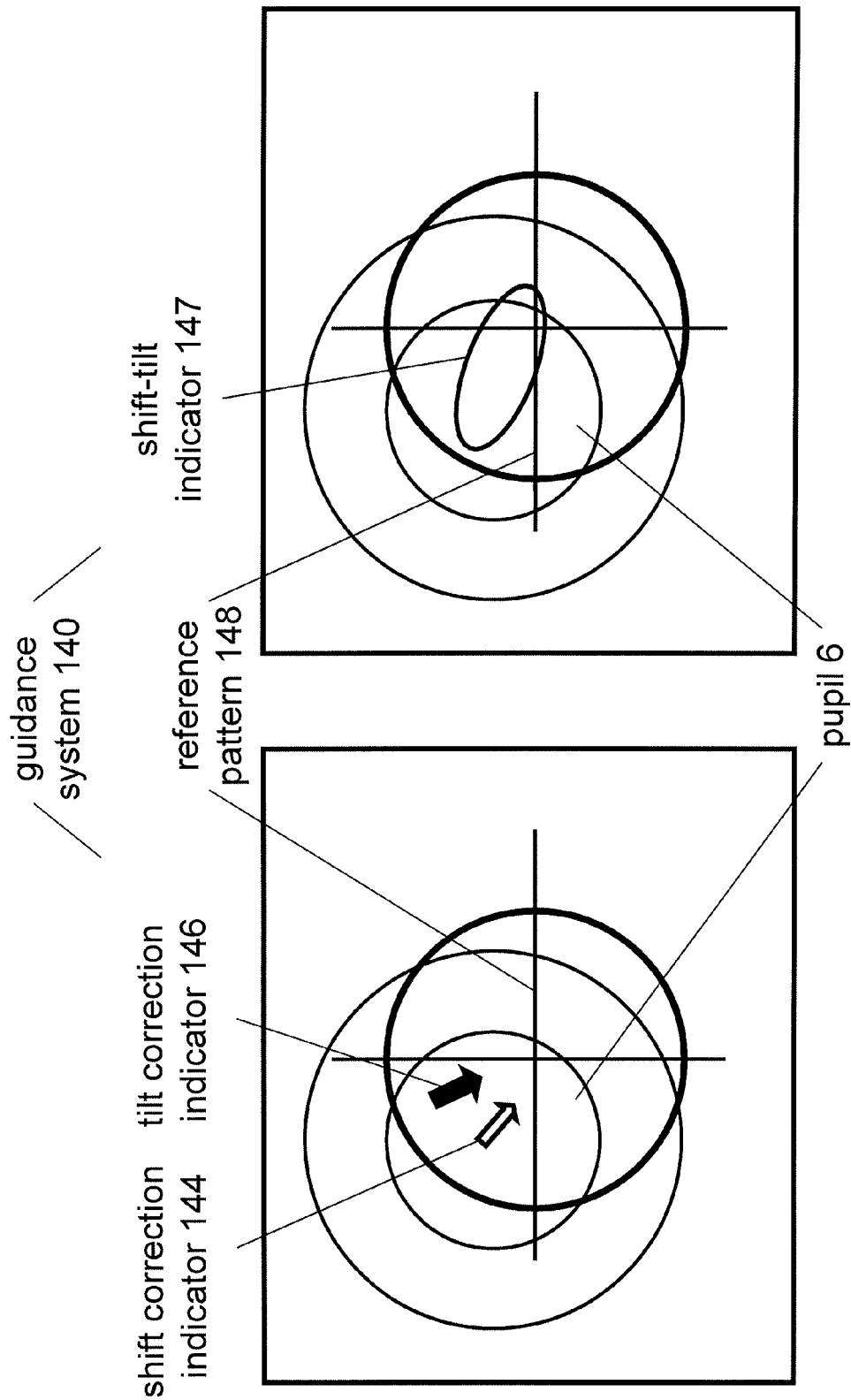

IMAGING-BASED GUIDANCE SYSTEM FOR OPHTHALMIC DOCKING USING A LOCATION-ORIENTATION ANALYSIS

TECHNICAL FIELD

This patent document relates to systems and techniques for ophthalmic docking. In more detail, this patent document relates to systems and methods for providing an imaging-based guidance system for docking an ophthalmic system to a patient's eye based on a location-orientation analysis.

BACKGROUND

The widespread introduction and acceptance of laser surgical systems in ophthalmic applications ushered in a new era of precision and control. One of the keys to achieving this high level of control is the immobilization of the eye relative to the laser surgical system. In many devices, the immobilization is carried out by affixing a patient interface to an objective of the laser and then docking it to the eye, often by vacuum suction. In other systems, a portion of the patient interface is docked to the eye, another portion to the objective, and then the surgeon gently aligns and locks the two portions together.

One of the factors the precision and utility of these systems depends on is the patient interface being docked to the eye in a central position. Such a central docking or centering can align an optical axis of the objective of the laser system and an optical axis of the eye. Since the laser beam is typically directed and controlled relative to the optical axis of the objective, aligning the optical axis of the eye with the optical axis of the objective by centering the docking can enable controlling the laser beam within the eye with high precision.

Centering the docking with the visible structures of the eye, such as the pupil or limbus is often a challenge, though, for multiple reasons. The patients sometimes move their eyes during docking, even against their own will. Also, even if the patient interface was centered with the eye at the beginning of the docking procedure, the globe of the eye can roll to one side during docking because of the pressure applied by the patient interface after contact has been made with the eye. Further, the shape of the eye structures can be an ellipsoid or irregular to some degree. Also, the limbus and the pupil are often not concentric. In these typical cases the center of the eye is not entirely well-defined: e.g. centering the patient interface with the pupil may not center it relative to the limbus.

An additional layer of complexity arises in systems intended for cataract procedures. The target of the cataract procedures is the lens, having limited visibility because it is an internal structure of the eye and it is essentially transparent. Moreover, the lens is typically not concentric with the visible structures of the eye, including the limbus and the pupil. For all these reasons, centering the patient interface with the limited visibility lens is hard. If the patient interface is centered with the visible limbus instead, this may also result in docking the interface misaligned with the limited-visibility internal lens. In this case, when during the cataract surgery the laser beam is referenced relative to the center of the patient interface aligned and docked with the limbus, the laser beam may be misdirected relative to the center of the lens, the intended target of the cataract surgery.

There can be several reasons for the lens being off-center. In many eyes the lens is anatomically off-center. Moreover, the pressure of the docking may also push and tilt the lens to one side as the lens is held in its place only by soft ciliary muscles.

Some systems compensate the lens being off-center by attempting to align the patient interface with the lens instead of the visible pupil. However, the transparency of the lens makes it difficult for the surgeon to determine the precise location and tilt of the lens and to align the patient interface accordingly.

Some systems employ an imaging system to image the lens to assist the alignment of the patient interface. However, the use of such imaging systems can encounter problems as well.

SUMMARY

A video-imaging system or a video-microscope can be used to assist the alignment of the patient interface and thus the docking. However, a video-microscope is primarily used to image the visible structures of the eye, such as the limbus and the pupil, and may not be able to image and assess the orientation of the lens, an internal and essentially transparent structure of the eye. Using an optical coherence tomography (OCT) system instead of the video-microscope has the advantage that OCT imaging systems can image the lens efficiently. However, the OCT imaging process is typically slow and does not provide the images fast enough to be useful for the docking process.

One way to accelerate the OCT imaging process is to image the target lens only selectively, thus producing images at a faster rate. Examples include scanning OCT systems that image the lens only along one dimensional scanning lines or circles instead of the full two dimensions, transverse to the optical axis. These scanning OCT imaging systems are able to generate images at a faster rate because they capture only limited or selected imaging information. Acquiring only limited imaging information, however, can cause other types of challenges when attempting to center the patient interface with the misaligned lens of the eye, as described next.

The lens can be misaligned with respect to the optical axis of the imaging system and thus the patient interface (PI) in different ways. The optical axis of the lens can be tilted relative to the optical axis of the PI, and the center of the lens can be shifted or displaced from the optical axis of the PI. The surgeon can analyze the OCT image and carry out compensating actions to compensate the lens-shift and the lens-tilt in order to align the patient interface with the lens.

To carry out these two types of compensating actions, the surgeon needs to identify the shift and the tilt separately from the OCT image of the lens. However, the limited imaging information provided by the faster scanning OCT systems typically convolutes information about the tilt and the shift. Therefore, when using a scanning OCT imaging system, the surgeon starts the docking process by attempting to analyze the scanning OCT image mentally to separate the tilt and shift of the lens.

During this separation attempt, the surgeon can determine that the lens is shifted by a certain distance in a certain direction from the PI optical axis and is tilted in a certain direction by a certain degree relative to it.

Once the shift is separated from the tilt, the surgeon can determine a direction and magnitude of a shift-compensating movement of a gantry of the laser system and move the gantry accordingly.

Subsequently, the surgeon can compensate the determined tilt of the lens as well. Since the optical axis in most imaging or laser systems cannot be tilted, the tilt-compensating action may include instructing the patient to rotate the surgical eye, manually rotating the eye ball, or adjusting a fixation light system. Since typically the first centering attempt leads only to an improvement of the alignment or compensation, these steps are often repeated in an iterative manner and in varying order or combinations.

If the surgeon was successful in separating and determining the shift and the tilt, then the result of the (possibly iterative) shift- and tilt-compensating actions is that the PI becomes well-centered with the lens. Therefore, the surgeon can proceed and dock the centered and aligned PI onto the eye.

However, there can be multiple problems with such "unprocessed-images" systems that do not process the images and thus provide no guidance for the surgeon. These problems include that separating the convoluted tilt and shift in the scanning OCT image mentally may not be easy to perform by the surgeon without computational processing and guidance under the intense time pressure of a surgical procedure. This can potentially lead to docking the PI on the eye in a non-centered position. Worse yet, the surgeon may even initiate adjustments that increase the misalignments instead of reducing them and therefore the iterative alignment process may not converge or converge only after several false steps.

A further inefficiency of "two-unprocessed-images" systems is that the OCT image of the lens is typically presented on a dedicated OCT display or screen, separate from the video microscope display. Therefore, in systems where the surgeon uses both an OCT and a video image for the alignment process, the surgeon has to analyze the lens image on the OCT display and the visible eye structures on the separate video display. The images on these two displays are typically from different points of view with different magnification and possibly using different reference conventions. Therefore, separating the shift and the tilt requires a challenging parallel analysis between two quite different images. The need to process and convert the two types of incongruent imaging information back-and-forth can overwhelm the surgeon, possibly undermining the efficiency of the centering and docking process.

To respond to these challenges, this patent document discloses imaging-guided docking systems that separate the tilt and shift and present them in an intuitive manner for the surgeon. In some implementations, an ophthalmic docking system can include an ophthalmic imaging system comprising an image processor, and a guidance system, coupled to the ophthalmic imaging system, wherein the ophthalmic imaging system is configured to image a portion of an eye of a patient, the image processor is configured to determine a location and an orientation of the imaged portion of the eye by analyzing the image, and the guidance system is configured to guide an ophthalmic docking based on the determined location and orientation.

The imaged portion of the eye can be a lens or another structure, feature or landmark of the anterior segment of the eye. The location and orientation can be determined relative to a variety of references, such as an optical axis of the imaging system, an internal reference mirror of the imaging system, an internal surface of an optical element of the surgical system, or an ophthalmic structure or layer of the anterior segment.

In other implementations, an ophthalmic docking system can include an ophthalmic imaging system, comprising an image processor, wherein the ophthalmic imaging system includes an in-depth ophthalmic imaging system configured to image an internal eye-structure of an eye of the patient, and a video-imaging system configured to video-image a frontal eye-structure of the eye, wherein the imaged portion of the eye comprises the internal eye-structure and the frontal eye-structure, and the image processor includes an in-depth image processor configured to determine an orientation of the internal eye-structure from the image of the internal eye-structure, and a video-image processor configured to determine a location of the frontal eye structure based on the image of the frontal eye-structure.

In some implementations, a method of guiding an ophthalmic docking can include imaging a portion of an eye of a patient with an ophthalmic imaging system, determining a location and an orientation of the imaged portion of the eye by analyzing the image with an image processor, and guiding an ophthalmic docking based on the determined location and orientation with a guidance system.

In some implementations, an ophthalmic docking system can include an ophthalmic imaging system, including an image processor, wherein the ophthalmic imaging system is configured to image a portion of an eye of a patient, and the image processor is configured to process the image to recognize an ophthalmic structure of the eye, and to determine a misalignment of the imaged portion of the eye relative to a reference; and a guidance system, coupled to the ophthalmic imaging system, configured to guide an ophthalmic docking based on the determined misalignment.

In some embodiments, an ophthalmic guidance system can include an ophthalmic imaging system, comprising an image processor, wherein the ophthalmic imaging system is configured to image a portion of an eye of a patient, and the image processor is configured to process the image to recognize an ophthalmic structure of the eye, and to determine a position of the imaged portion of the eye relative to a reference; and a guidance system, coupled to the ophthalmic imaging system, configured to guide an ophthalmic ultrasound-based surgical procedure based on the determined position.

BRIEF DESCRIPTION OF THE DRAWINGS

FIGS. 7A-B illustrate the video-microscope display of the shift and tilt indicators.
FIGS. 9A-C illustrate stages of the compensation of a shift and a tilt misalignment.
FIGS. 10A-B illustrate two additional implementations of the video-microscope display.

DETAILED DESCRIPTION

Implementations and embodiments in this patent document provide an ophthalmic docking system that includes an imaging system, capable of separating and identifying a shift and a tilt of a patient's eye and can present the shift and tilt information in an integrated, congruent manner to avoid overwhelming the surgeon. Such a docking system may be helpful to increase the precision and ease of the docking of a patient interface of an ophthalmic surgical system to the eye, such as a laser cataract surgical system.

Figure 1A:
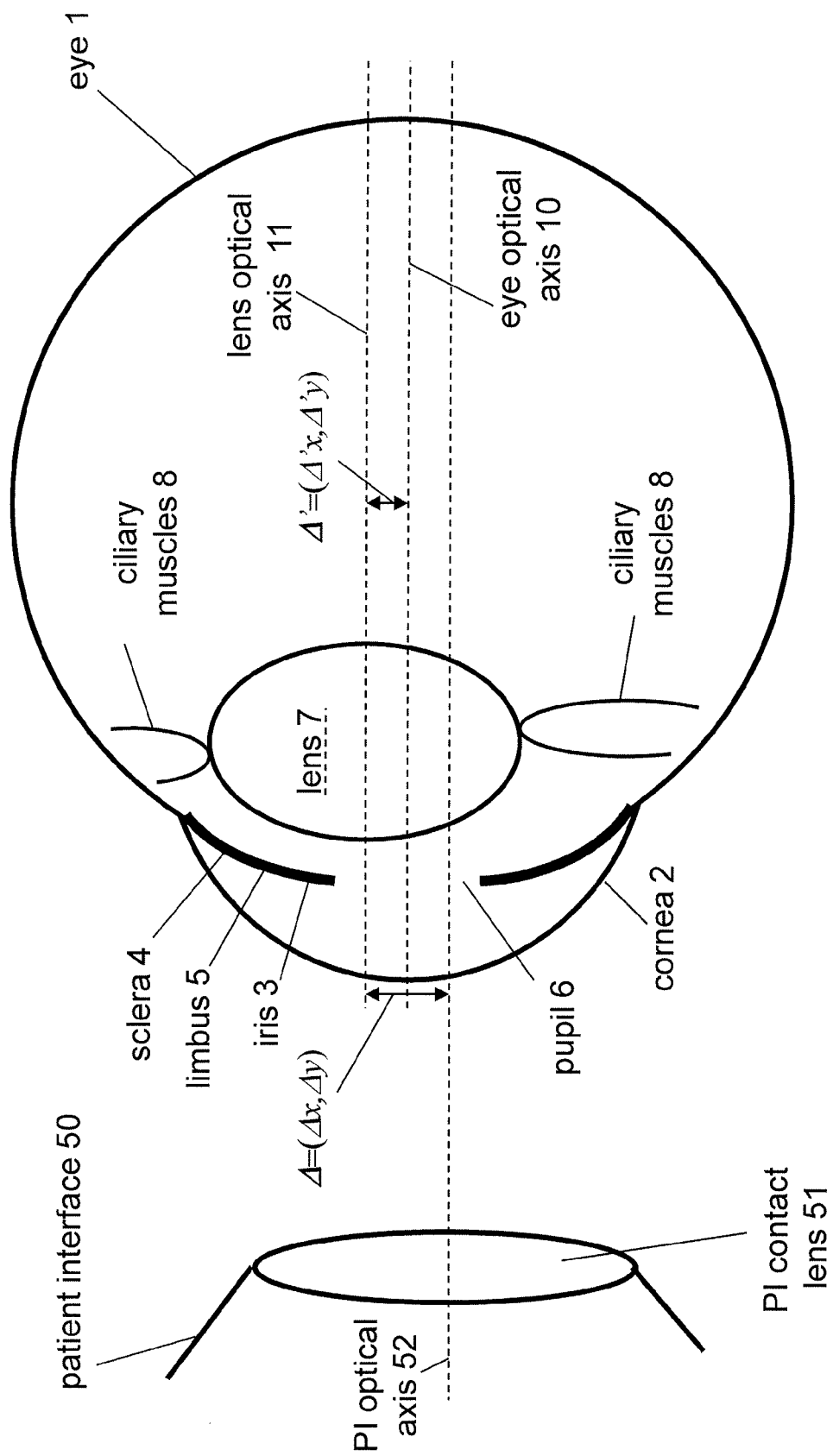
FIGS. 1A-B illustrate various misalignments of the eye.
Figure 1B:
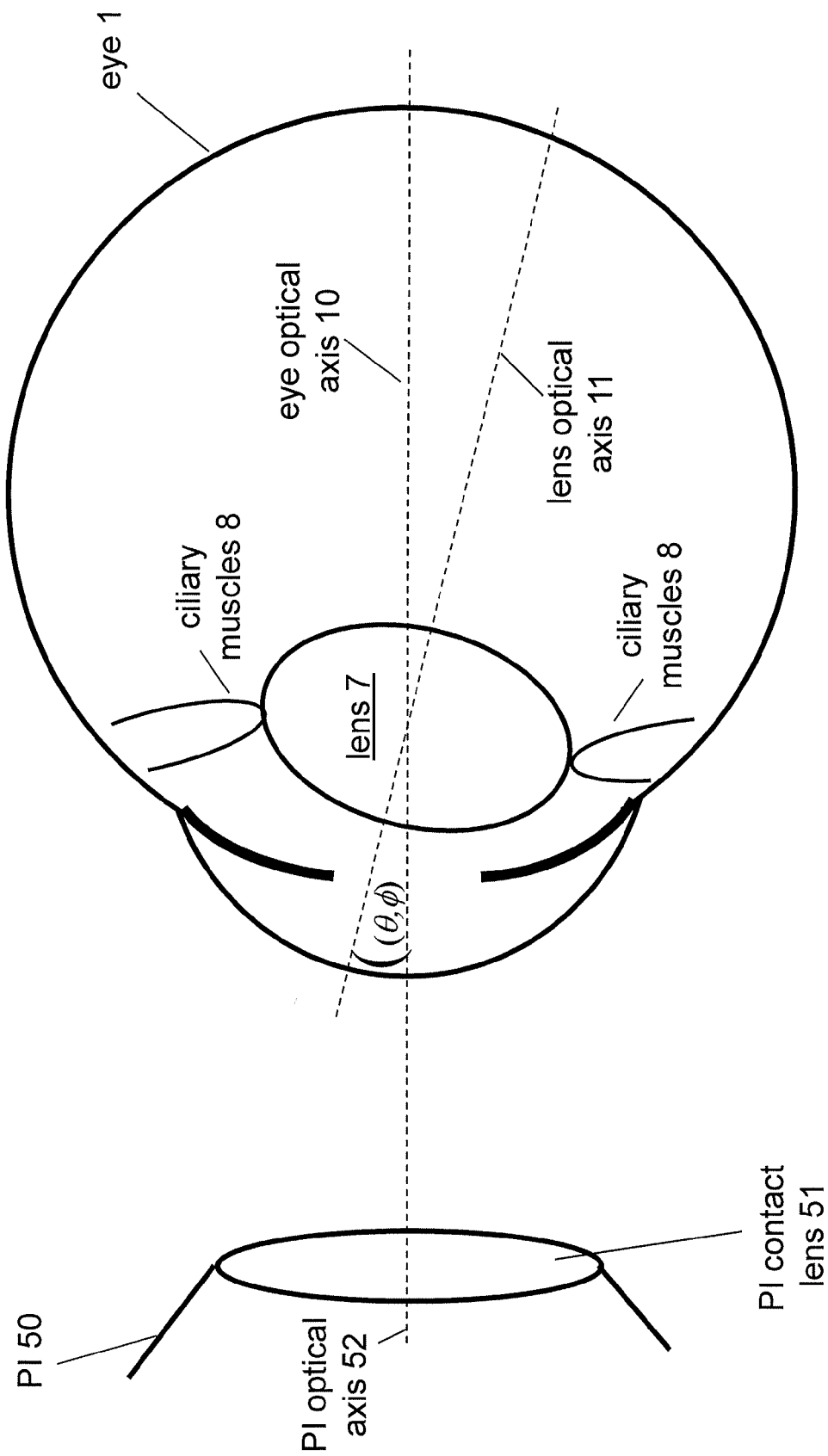

FIGS. 1A-B illustrate various misalignments of a patient interface (PI) 50 and its PI contact lens 51 relative to an eye 1. The well-known structures in the eye 1 include a cornea 2, an iris 3, a sclera 4, separated from the iris 3 by the limbus 5. An opening of the iris 3 defines a pupil 6. A lens 7 is an internal structure of the eye 1, held in its place by the soft ciliary muscles 8.

FIG. 1A illustrates that, as described above, the lens 7 can be shifted from an optical axis 10 of the eye 1 for a variety of reasons, so that a lens optical axis 11 of the lens 7 is shifted from the eye optical axis 10 by a transverse vector $\Delta'=(\Delta'x, \Delta'y)$ and thus from a PI optical axis 52 of the PI 50 by a transverse vector $\Delta=(\Delta x, \Delta y)$. For simplicity, these transverse displacement or shift vectors will be simply referred to as $\Delta'$ and $\Delta$.

FIG. 1A illustrates one of the challenges of guiding a docking system by traditional methods. Even if a surgeon aligns and centers the patient interface 50 with the eye optical axis 10 as defined by the visible structures of the eye 1 such as the pupil 6, the lens optical axis 11 of the hard-to-see internal lens 7 can remain shifted from the PI optical axis 52 of the patient interface 50.

FIG. 1B illustrates another form of misalignment of the lens 7 and the patient interface 50. Even if a center of the lens 7 lies on the eye optical axis 10 and even if the eye optical axis 10 coincides with the PI optical axis 52, the lens optical axis 11 can still remain tilted relative to the PI optical axis 52. In general, this tilt can be described by the Euler angles $\phi=(\theta,\phi)$, which will be collectively referred to as the tilt angle $\phi$.

Figure 1C:
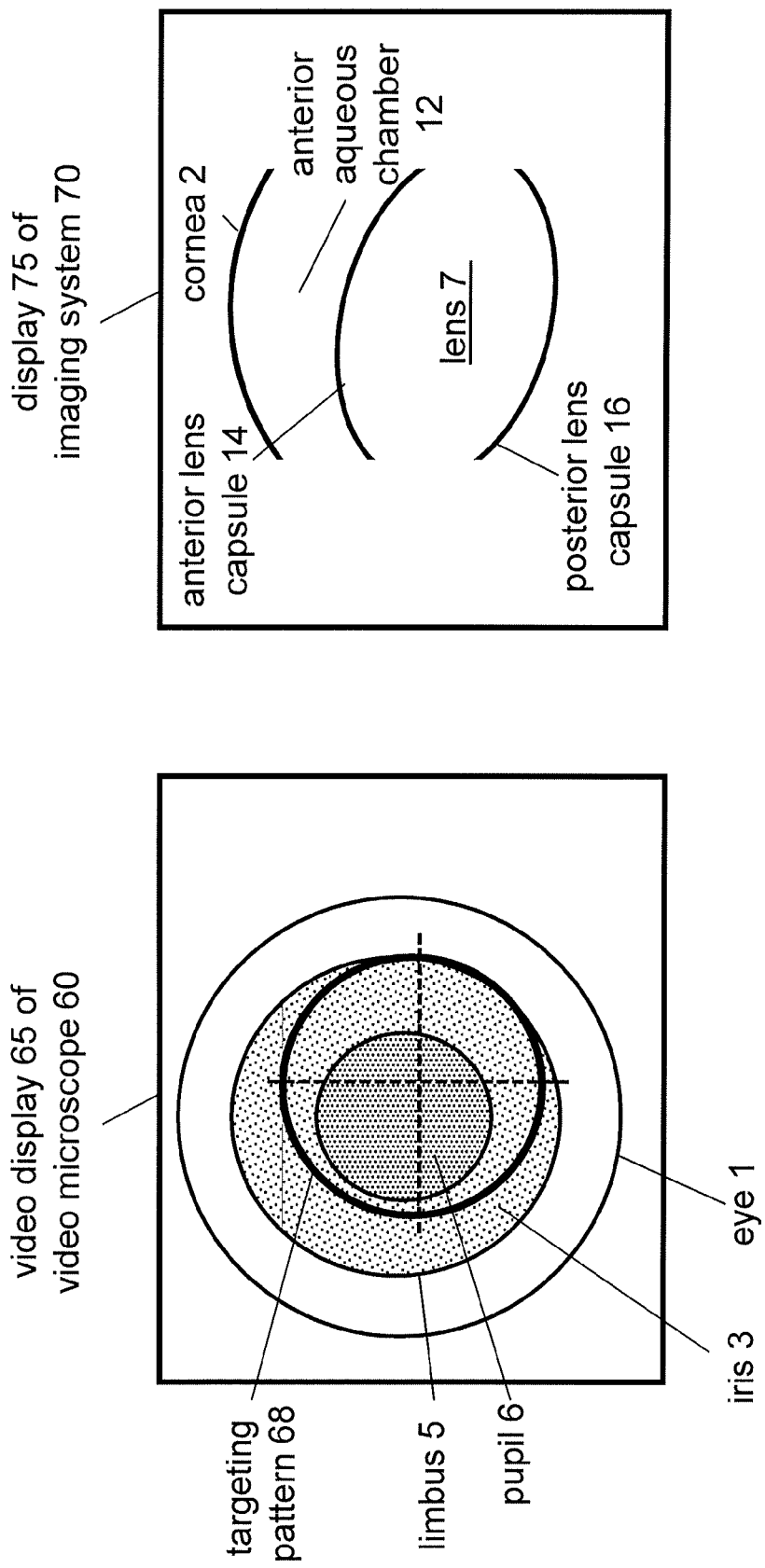
FIG. 1C illustrates the two displays of a "two-unprocessed-images" system.

FIG. 1C illustrates how a misaligned or off-center eye 1 can appear on a video display 65 of a video-microscope 60. Such video-microscopes 60 often display a targeting pattern 68 to guide the surgeon to align or center the PI 50 with the eye 1.

Some "two-unprocessed-images" systems may provide a second image to guide the surgeon docking the PI 50: an imaging system 70 can provide a cross sectional or scanning view of the eye 1, shown in a separate imaging display 75. The cross-sectional view can show the cornea 2 and the lens 7, separated by an anterior aqueous chamber 12. The lens 7 can be enveloped by an anterior capsular layer 14 and a posterior capsular layer 16. During ophthalmic procedures often muscle relaxants are administered that relax the iris 3 thus enlarging the pupil 6. At least for this reason the expanded pupil 6 often does not even appear on cross sectional or scanning images.

As described before, when operating such "two-unprocessed-images" systems, the surgeon is expected to analyze the cross sectional image on the display 75 in combination with the video image of the video display 65, mentally separate the tilt and the shift of the lens 7 and then perform compensating actions, monitoring them on the display 65 of the video microscope 60. However, repeatedly moving back and forth between the two different types of images and translating the image information accordingly without computational processing and guidance can be quite overwhelming and time consuming for the surgeon.

Figure 2:
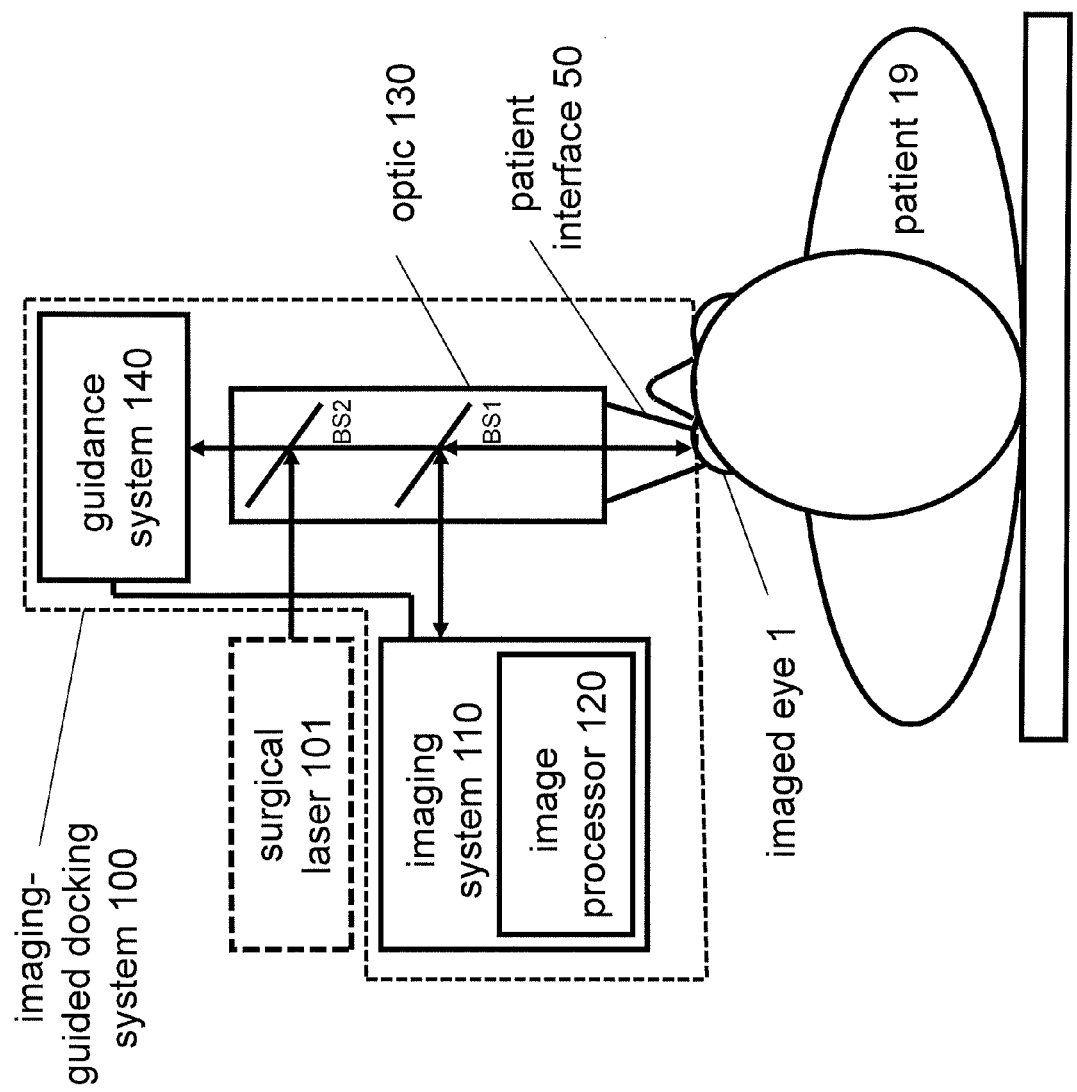
FIG. 2 illustrates an imaging-guided docking system.

FIG. 2 illustrates an imaging-guided ophthalmic docking system 100 that may facilitate a simplified and more efficient imaging-guided docking. The docking system 100 can include an ophthalmic imaging system 110 that may include an image processor 120, where the ophthalmic imaging system 110 can be configured to image a portion of the eye 1 of a patient 19. The imaging can be performed in a variety of ways. For example, an imaging beam can be generated by the imaging system 110, then coupled into an optic 130 of the docking system 100 through a beam-splitter BS1 and directed into the eye 1. The returned imaging beam, returned from the eye 1, can be redirected or deflected by the same beam-splitter BS1 into the imaging system 110 to form an image of the eye 1.

The image processor 120 can be configured to determine a location and an orientation of the imaged portion of the eye by analyzing the image generated from the returned imaging beam. The location can be expressed in terms of a shift $\Delta$ relative to a reference such as the PI optical axis 52, and the orientation can be expressed in terms of a tilt $\phi$ relative to the PI optical axis 52.

The imaged portion can include parts of an internal structure of the eye and parts of its frontal or visible structures. For example, FIG. 1C illustrates the case when the imaged portion of the eye includes a portion of the cornea 2, a portion of the anterior capsular layer 14 and a portion of the posterior capsular layer 16. In other implementations, the imaged portion of the eye can include a lens-capsular layer, a lens target region, the lens 7, a hardened nucleus of the lens 7, the limbus 5, the iris 3, the pupil 6, a corneal endothelium, a corneal epithelium, or an ophthalmic structure in the anterior segment of the eye 1, among others.

The docking system 100 can also include a guidance system 140, coupled to the ophthalmic imaging system 110, configured to guide an ophthalmic docking based on the determined location and orientation. The guidance system 140 can include a video display of a video microscope or a display of the imaging system 110. The guidance system 140 can be configured to guide the ophthalmic docking by displaying images and guidance information for an ophthalmic surgeon.

The docking system 100 can be part of a larger ophthalmic system that can perform other functions as well. For example, the docking system 100 can be integrated with a surgical laser 101, where a surgical laser beam of the surgical laser 101 can be coupled into the optic 130 at a beam splitter BS2 to be directed to the eye 1. The surgical laser 101 can perform cataract procedures, such as a fragmentation of the lens 7 or a lysis of the lens 7. It can also perform procedures in the cornea, such as creating limbal relaxing cuts or creating access cuts for an ultrasound phaco-tip. The surgical laser 101 can also perform LASIK related procedures, including flap-cuts in the cornea 2.

The docking system 100 can be also part of a larger or more complex imaging system, such as a surgical microscope which, however, does not perform a surgical procedure. Instead, it may perform an imaging of a portion of the anterior segment of the eye 1. Finally, the docking system 100 can be part of a variety of diagnostic systems, for example in the form of an alignment system that does not necessarily involve direct physical contact with the eye.

The ophthalmic imaging system 110 can include a wide variety of imaging systems, such as a time domain optical coherence tomography (OCT) system, a frequency domain OCT system, a spectrometer-based OCT system, an ultrasound-based system, a microscope based system, an electronic imaging system, a digital imaging system, a Purkinje imaging system, a structural illumination system, a slit lamp system, or a Scheimpflug imaging system. The possibly substantial differences between these imaging systems will be discussed below.

The ophthalmic imaging system 110 can include a scanning imaging system to perform a scan by directing an imaging beam to points of at least one of an arc, a line, a loop, a circle, an ellipse, a star, a line with repeated features, a two dimensional pattern and a two dimensional mesh. The imaging system 110 can image the imaged portion of the eye in a depth-range at points of the scan.

Implementations of image-guided ophthalmic docking systems which can be advantageously combined with the here-described imaging-guided ophthalmic docking system 100 have been described in the jointly owned patent document: "Image-Guided Docking for Ophthalmic Surgical Systems" by A. Juhasz and K. Vardin, USPTO patent application Ser. No. 12/815,179, hereby incorporated in its entirety by reference.

Figure 3A:
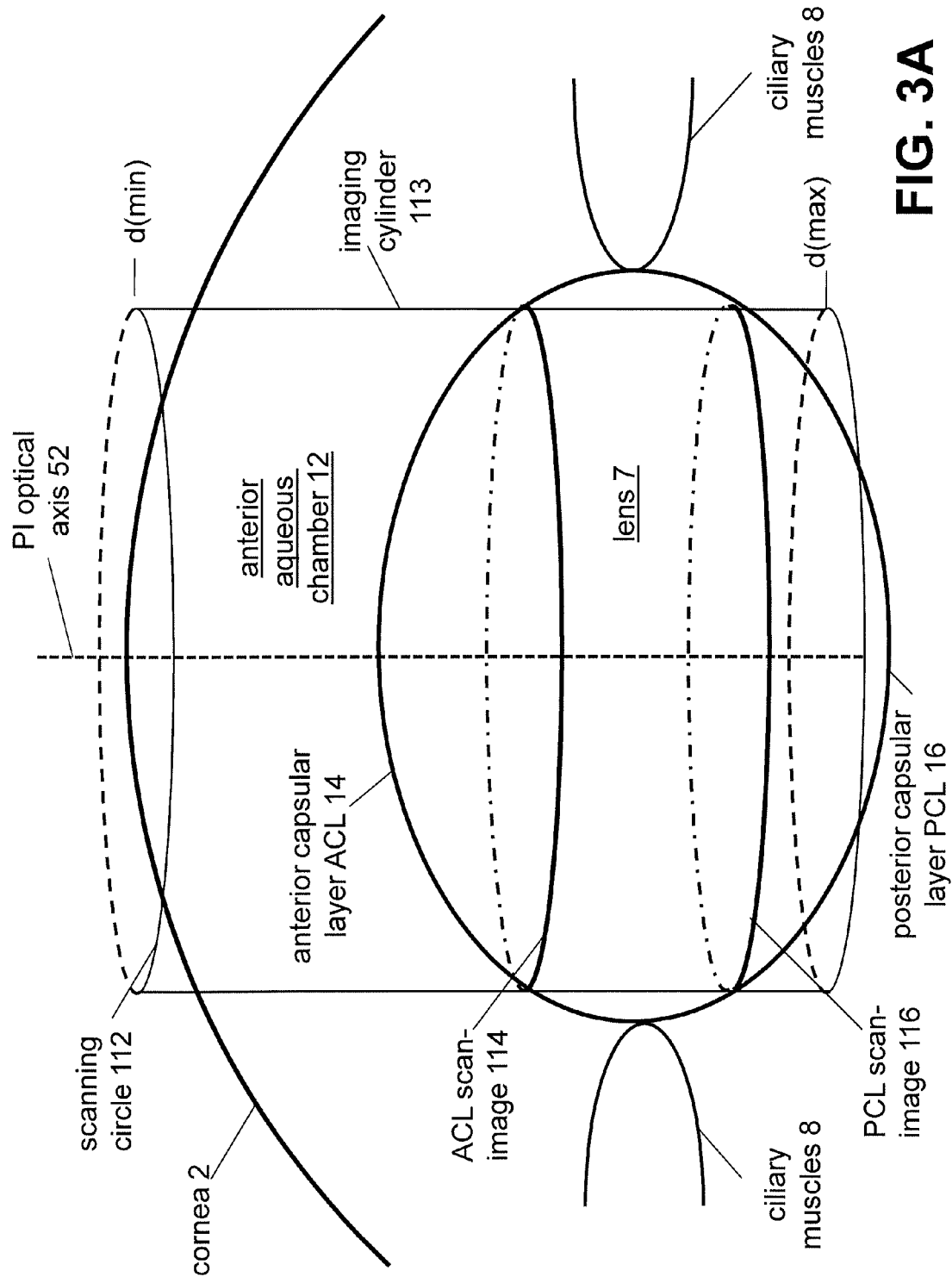
FIGS. 3A-B illustrate a scan and an OCT image of a fully aligned lens.

FIG. 3A illustrates an implementation of the imaging system 110. The imaging system 110 can include e.g. a spectrometer based OCT (SB-OCT) system, directing an imaging beam to (x,y) points of a scanning circle or loop 112, typically oriented transverse to the PI optical axis 52. As the imaging laser beam is returned from a specific (x,y) point of the scanning circle 112, it carries imaging information about the ophthalmic structures sharing the same (x,y) transverse coordinates from all depths d within a depth-range between a minimal depth d(min) and a maximal depth d(max)–sometimes called an A-scan. It is noted that time domain OCT systems acquire the A-scan imaging information from different depths sequentially, whereas spectrometer based OCT systems acquire the A-scan imaging information from all depth simultaneously. Here the depth d can be measured from different reference points, including a reference mirror of the SB-OCT system, a reference point internal to the optic 130, a distal surface of the PI contact lens 51 in contact with the cornea 2, or even from an ophthalmic structure or landmark inside the eye 1. Some ophthalmic imaging systems are capable of collecting and returning imaging information from an imaging range between a minimal depth d(min) that is essentially zero micron, 0µ, measured from the PI contact lens 51, capturing corneal imaging information, to a maximal depth of d(max)=5,000µ, 7,000µ, or even 10,000µ, capturing imaging information covering most of the anterior segment of the eye up to the posterior capsular layer 16.

The A-scans of the eye taken at subsequent (x,y) points along the scanning circle 112 can be integrated into a scan-image of the eye, sometimes called a B-scan. A B-scan in essence unfolds the image of the eye from an imaging cylinder 113 defined by the scanning circle 112 and the d(min)-d(max) imaging range. This unfolded image can be labeled or indexed by a scanning variable: a length along the scanning circle 112 or an angular scanning variable α, defined e.g. in radians.

Figure 3B:
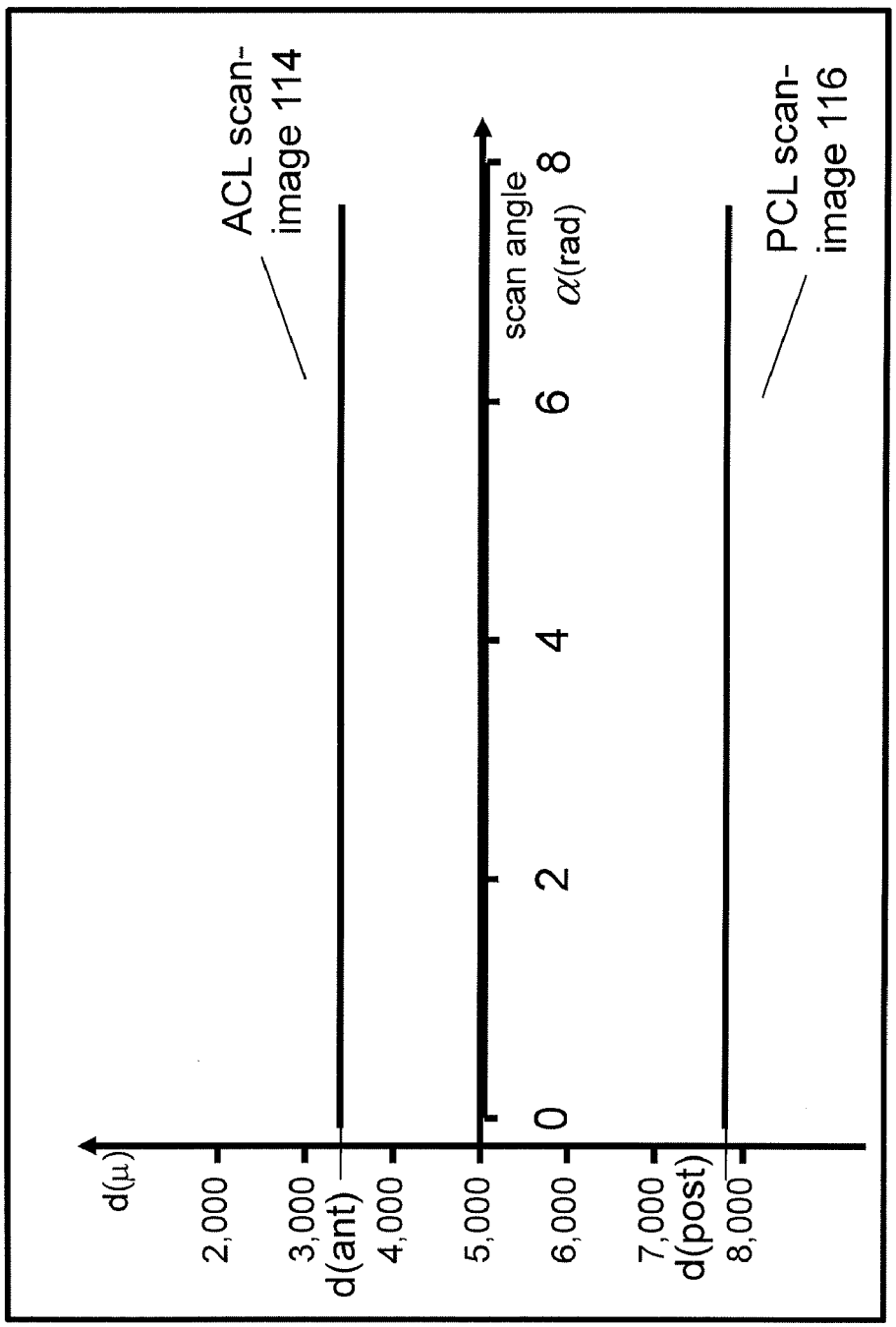

FIG. 3B illustrates an image or B-scan of a fully aligned and centered lens 7, unfolded from the imaging cylinder 113. Visibly, the scanning beam located the anterior capsular layer (ACL) 14 at a depth d(ant) along the entire circular scan, thus generating an ACL scan-image 114 that is a horizontal line at a depth of d=d(ant) of about 3,400µ in this example along the entire 2π radian range of the angular scanning variable α. Analogously, a posterior capsular layer (PCL) scan-image 116 on the imaging cylinder 113 is a horizontal line at d=d(post) of about 7,800µ. For simplicity and clarity, the image of the cornea 2 at a depth close to d=0µ is not shown.

As mentioned above, one of the challenges of the "two-unprocessed-images" systems of FIG. 1C is that they provide the surgeon with a video-microscope image and a different-looking cross-sectional or scanning OCT image and prompt the surgeon to quickly analyze these incongruent images to separate and determine the shift and tilt of the lens 7. These tasks are quite demanding and can potentially overwhelm the surgeon, especially under the time pressure of the surgery.

Implementations of the imaging-guided docking system 100 can reduce this problem by the ophthalmic imaging system 110 not only displaying the image for the surgeon for analysis, but in addition the imaging system 110 itself performing an image recognition process on the image. The image recognition process may be able to recognize the ACL and PCL within the noisy raw image and generate the corresponding ACL scan-image 114 and the PCL scan-image 116. Once the ACL and PCL scan-images 114 and 116 have been generated by the imaging system 110, the image processor 120 can analyze the generated images to computationally separate the shift and the tilt of the lens 7, and the guidance system 140 can display the determined shift and tilt in a manner convenient for the surgeon, thus relieving the surgeon from the hitherto required mental analysis.

The convenient display by the guidance system 140 can, e.g., integrate the shift and tilt information into the same video-microscope image. In other cases, a second image can be displayed separately but in a manner congruent with the image on the video-microscope, wherein the second image could show the tilt information and the video-microscope image the shift information. The second image can be displayed on the same display as the video image, only in a different region of the display, or on a separate second display.

Performing the image-recognition process by the image processor 120 can play a useful role as in a raw OCT image the ACL/PCL 14/16 may appear only as regions of image points reflecting the light somewhat more than their neighboring regions. But the contours of these more reflecting regions are often not defined too clearly, especially if the imaging noise is substantial, or if there is a systematic noise, or there are additional image lines, or if some image lines cross or artifacts are present in the image.

To recognize the capsular layers even in a noisy image and to determine the tilt and shift of the lens, in some implementations the image processor 120 can be configured to analyze the scan-images of the recognized layers by using a geometric model of the lens 7 to determine a location and an orientation of the lens 7. For example, the image processor 120 can attempt to fit a sphere, an ellipsoid or elliptical curves to the regions of enhanced reflection, and recognize the reflecting regions as the scan-images of capsular layers if they can be fit sufficiently well with the sphere or ellipsoid of the geometric model. The edges of the regions can be determined, for example, as the points where the gradient of the image intensity exhibits a local maximum. A wide variety of analogous image recognition approaches can be implemented as well. The misalignments and their analysis will be described in the context of the following figures.

Figure 4A:
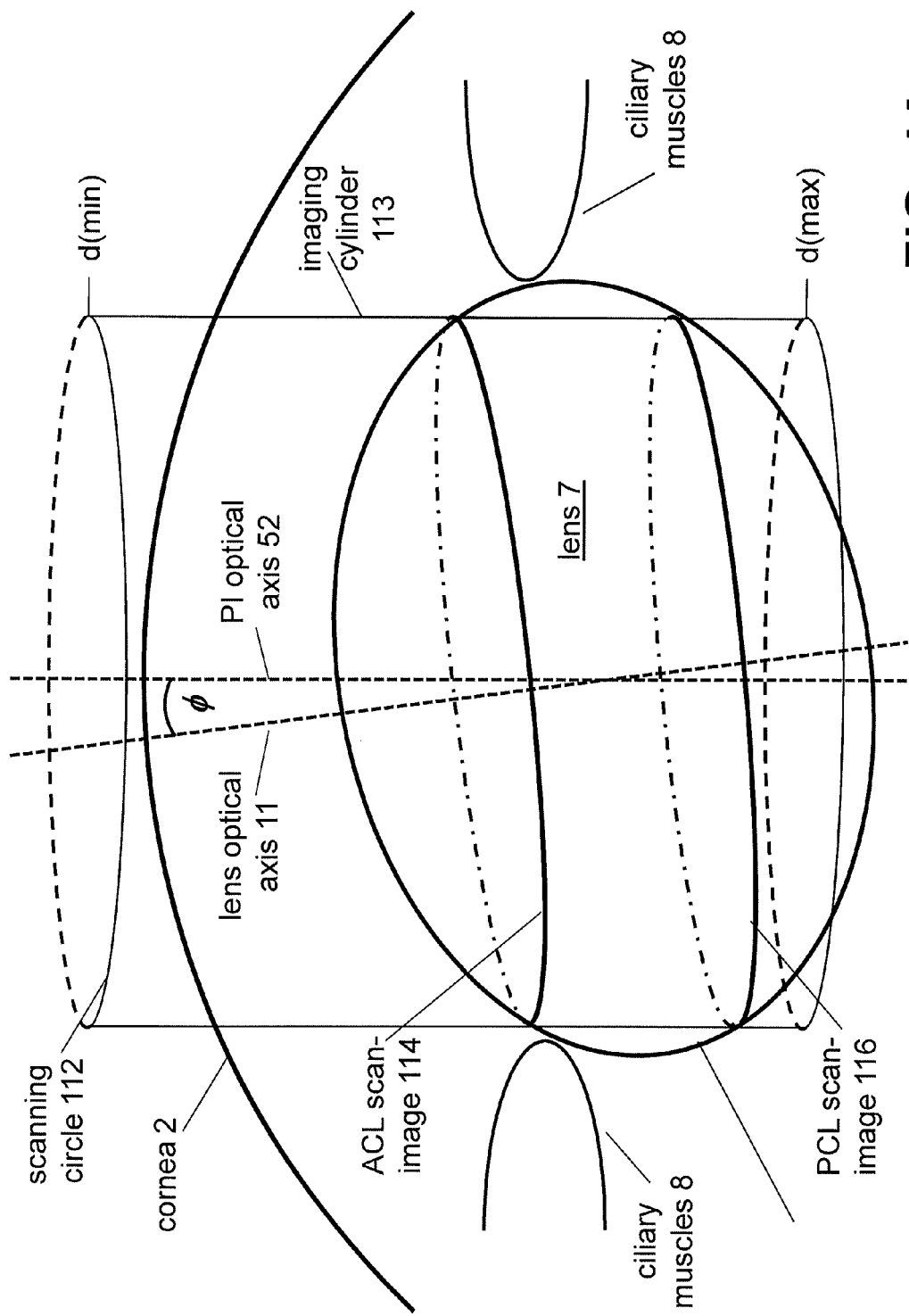
FIGS. 4A-B illustrate a scan and an OCT image of a tilted lens.

FIG. 4A illustrates a "pure tilt" situation when the center of the lens 7 is on the PI optical axis 52, but the lens optical axis 11 is tilted relative to the PI optical axis 52 by a tilt angle φ.

Figure 4B:
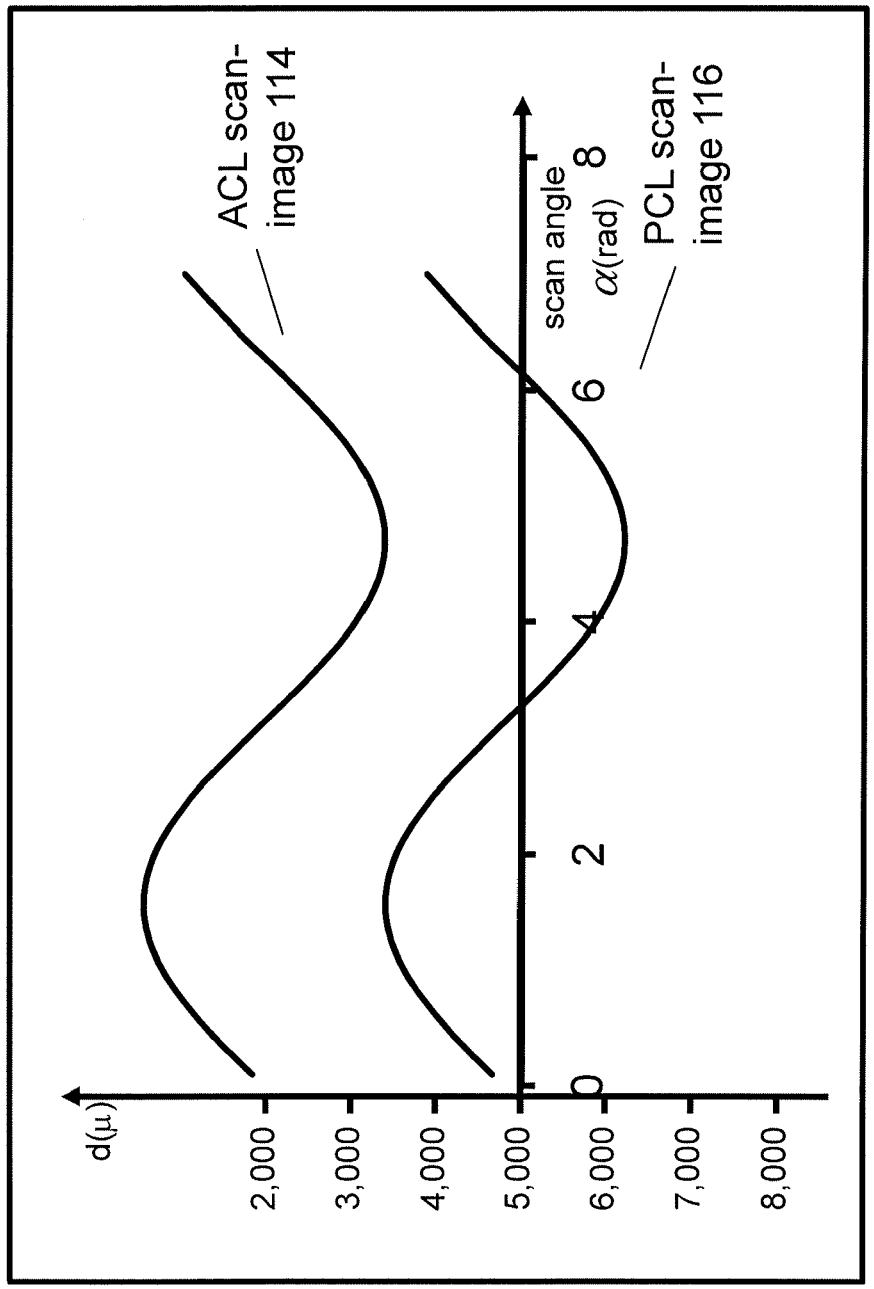

FIG. 4B illustrates that in misaligned situations the scan-images of the capsular layers are often sinusoidal lines as a function of the angular scan variable, angle, or phase α. For example, in the "pure tilt" situation of FIG. 4A the ACL scan-image 114 and PCL scan-image 116 can be sinusoidal lines that are "in-phase" as a function of the angular scan variable α, as seen from their maxima being aligned along the scan angle α.

Figure 5A:
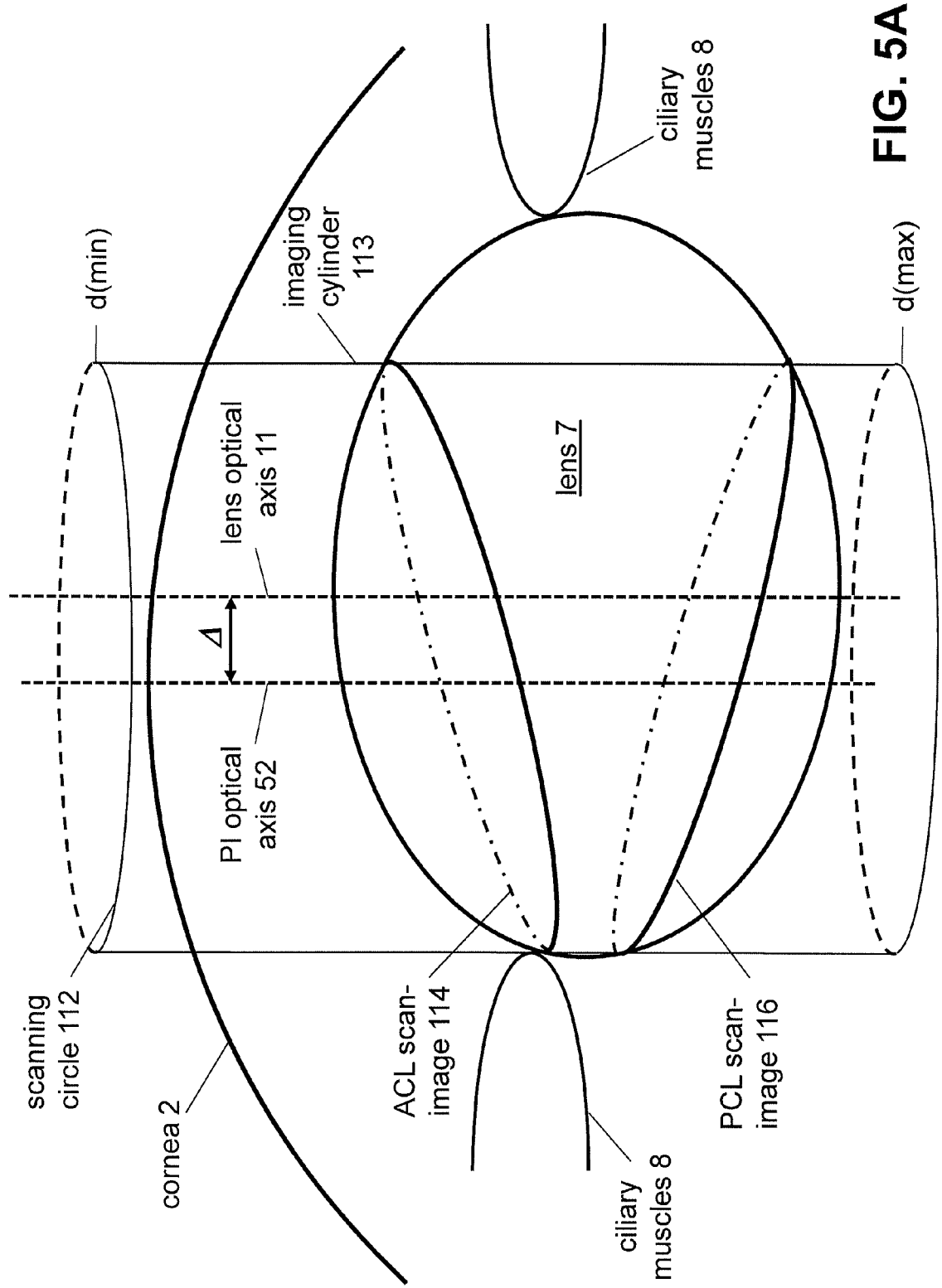
FIGS. 5A-B illustrate a scan and an OCT image of a shifted lens.

FIG. 5A illustrates a "pure shift" situation, when the lens optical axis 11 is aligned with the PI optical axis 52, but the center of the lens 7 is shifted from the PI optical axis by a shift Δ.

Figure 5B:
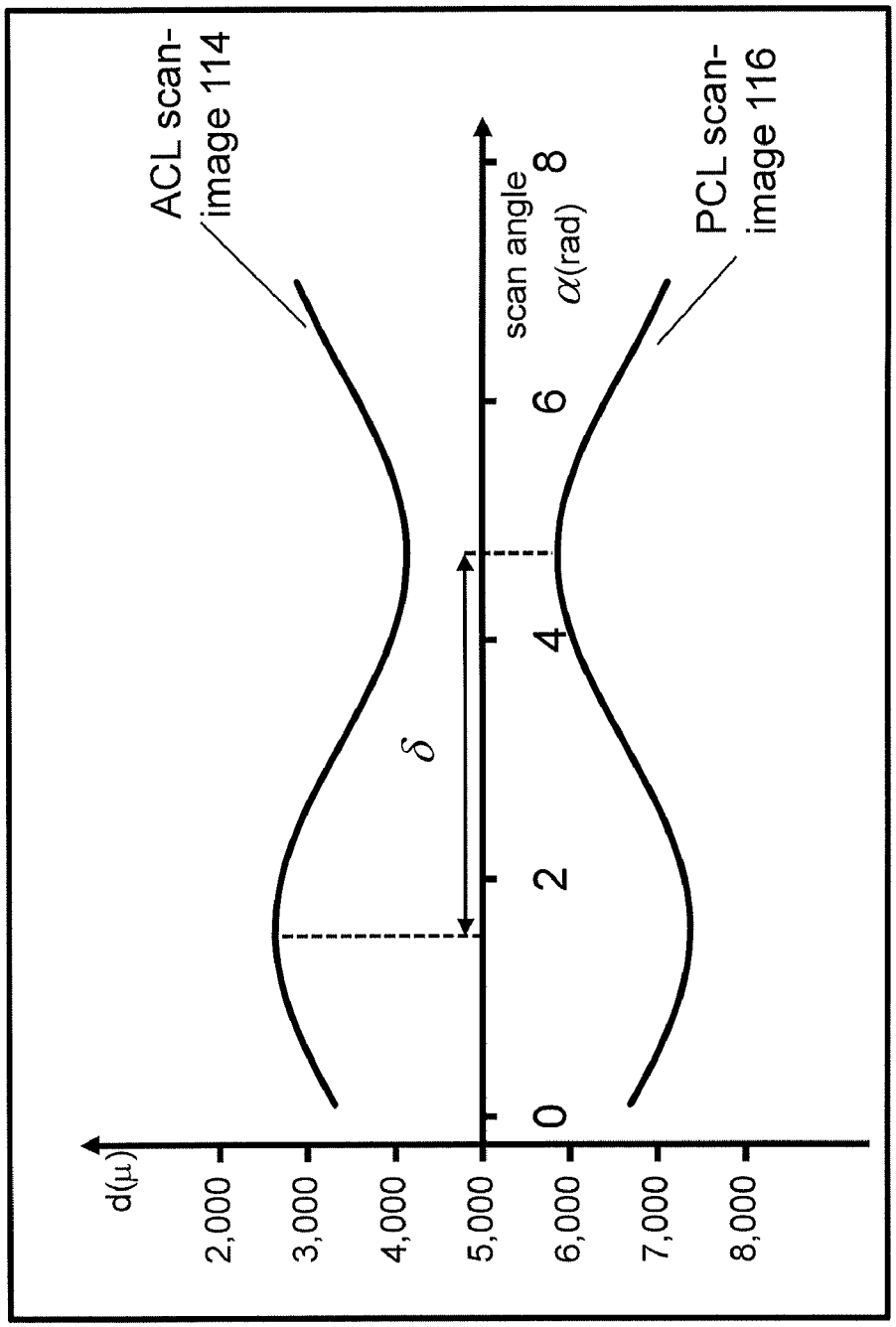

FIG. 5B illustrates that in this pure shift situation the ACL scan-image 114 and the PCL scan-image 116 can still be sinusoidal, but they are "out-of-phase" relative to each other by a phase shift of δ=π radians. This phase shift δ causes the maximum of the ACL scan-image 114 being aligned with the minimum of the PCL scan-image 116. Typically, the phase shift δ can be related to the tilt angle φ by geometric relations.

It is also noted that the image-amplitudes or the minimum and maximum depths of the ACL and PCL scan-images 114 and 116 can be related to the tilt angle φ and shift Δ by geometric relations.

Figure 6:
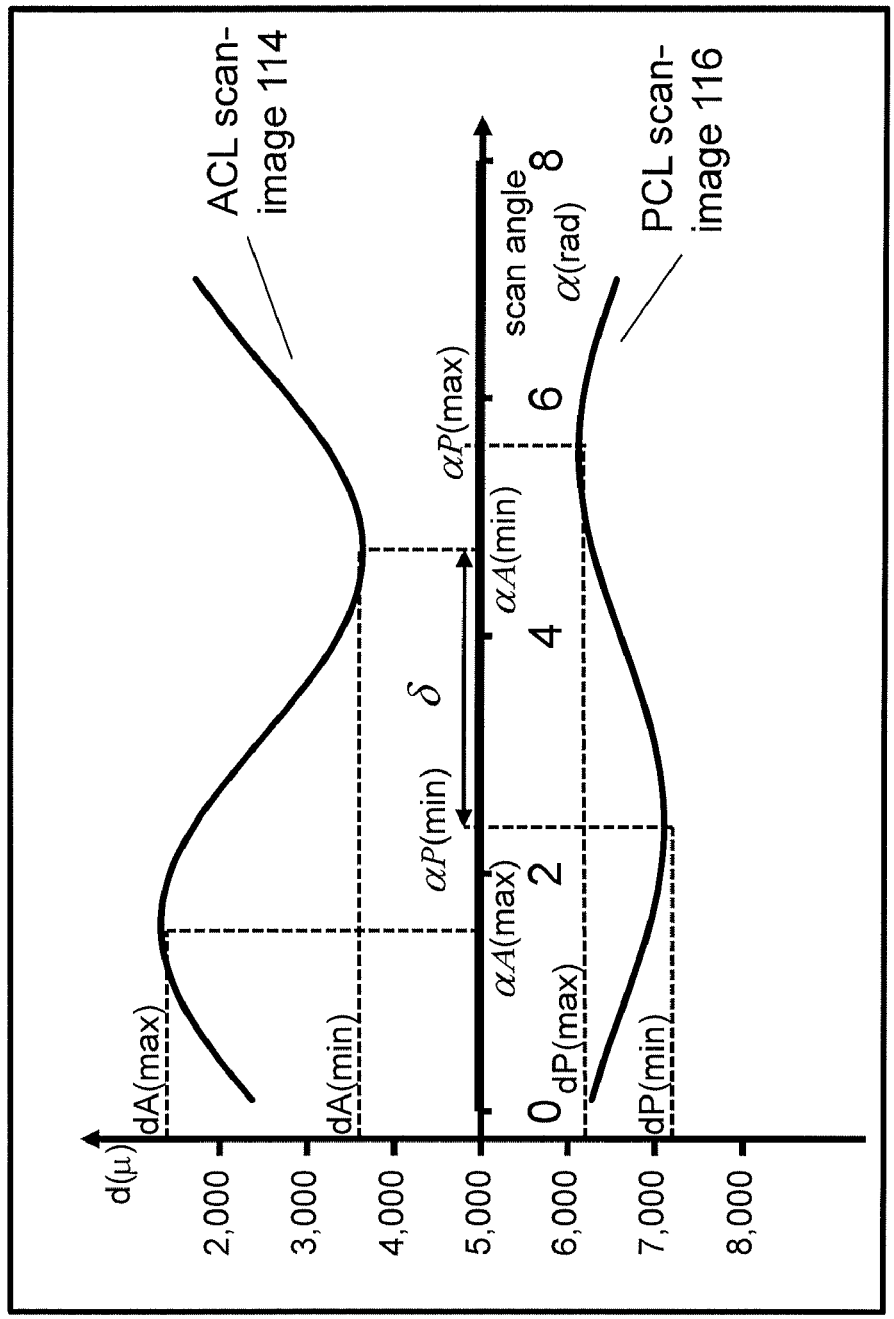
FIG. 6 illustrates a scanning OCT image of a lens, both tilted and shifted.

FIG. 6 illustrates that in a generic situation when the lens 7 is both shifted and tilted, the ACL/PCL scan-images 114/116 exhibit a combination of the pure tilt and pure shift images. Correspondingly, the ACL scan-image 114 and the PCL scan-image 116 can be separated by a general phase shift δ=αA(min)−αP(min). The phase shift δ is also equal to δ=αA(max)−αP(max) when measured past 2π in FIG. 6. Here, αA(min) refers to the scan angle, or phase, a where the ACL scan-image 114 has its minimum dA(min) and thus its lowest or deepest depth. The other terms, αP(min), αA(max) and αP(max), are defined analogously in the context of the ACL/PCL scan-images 114/116.

More generally, the image processor 120 can be configured to determine not only the extrema of the ACL/PCL images 114/116, but to follow any number of procedures to determine an anterior phase and an anterior amplitude of the scan-image 114 of the anterior capsular layer and a posterior phase and a posterior amplitude of the scan-image 116 of the posterior capsular layer, and to determine the location and the orientation of the lens from the anterior phase, the anterior amplitude, the posterior phase and the posterior amplitude.

For example, the image processor 120 can determine a characteristic anterior phase αA of the ACL scan-image 114, such as αA(min) or αA(max), as well as the corresponding characteristic anterior amplitudes or image depths dA, such as the depths dA(min) or dA(max), corresponding to the above anterior phases αA(min) or αA(max). Furthermore, the image processor 120 can also determine a characteristic phase αP of the PCL scan-image 116, such as αP(min) or αP(max), as well as a characteristic image depth dP, such as the corresponding depths dP(min) or dP(max).

With these phases and amplitudes, the image processor 120 can proceed and determine the unknown components (Δx, Δy) of the shift vector Δ and the unknown Euler angles (θ,φ) of the tilt angle φ from an analysis of various combinations of the above determined phases and depths or amplitudes:

$$(\Delta x, \Delta y, \theta, \phi) = F1(\alpha A, dA, \alpha P, dP), \quad (1)$$

where F1 is a function of its arguments which can be various combinations or pairings of the determined scan angles and depths corresponding to the depth maxima or minima of the ACL/PCL scan images 114/116.

As mentioned before, the analysis may involve using a model of the capsular layers. For example, the analysis may assume that the capsular layers 14 and 16 can be modeled as portions of a sphere or an ellipsoid, and then proceed to determine the parameters of the sphere or ellipsoid by fitting the ACL/PCL images 114/116 with the sphere or ellipsoid.

There is a large number of alternative ways to carry out this analysis. Some techniques that can be advantageously implemented for this analysis were already described in the jointly owned patent document: "Imaging Surgical Target Tissue by Nonlinear Scanning" by I. Goldshleger et al., USPTO patent application Ser. No. 12/619,606, hereby incorporated in its entirety by reference.

Examples of alternative analyses include the image processor 120 determining the anterior maximum depth dA(max) and the anterior minimum depth dA(min) of the ACL scan-image 114, and the posterior maximum depth dP(max) and the posterior minimum depth dP(min) of the PCL scan-image 116 along the scan variable α, and determining the shift and tilt from these extrema:

$$(\Delta x, \Delta y, \theta, \phi) = F2(dA(\min), dA(\max), dP(\min), dP(\max)), \quad (2)$$

where F2 is another function of its arguments.

The scan angles and depths can be determined, selected and analyzed according to numerous other criteria. While the corresponding functions Fn(x1, . . . xm) (where m can be 2, 3, 4 or more) and the details of the analysis may proceed differently, the overall scheme of extracting the shift Δ and tilt φ remains the same.

In some implementations, the image processor 120 can be configured to determine a phase and an amplitude of only one of the capsular layer scan-images, and from those to determine a location or shift and an orientation or tilt of the lens 7.

FIGS. 7A-B illustrate that the guidance system 140 can include a display unit 142 such as a video-microscope display 142. The guidance system 140 can be coupled to the image processor 120 so that the display unit 142 can display a location or shift misalignment indicator based on the determined location of the imaged portion of the eye, and an orientation or tilt misalignment indicator based on the determined orientation of the imaged portion of the eye, both determined by the image processor 120 processing the SB-OCT image by one of the above methods. The eye 1 itself can be indicated only very schematically, with only the pupil 6 and the iris 3 explicitly shown and the shading suppressed for clarity.

In general, the location misalignment indicator can include an eye location or shift indicator 144 based on the determined location of the imaged portion of the eye, and a location or shift reference or reference pattern 148-s. An operator of the docking system 100 can reduce the shift misalignment of the imaged portion of the eye by aligning the eye location or shift indicator 144 with the location reference 148-s. In embodiments where the imaged portion of the eye includes the lens 7, embodiments of the eye location or shift indicator 144 can represent a lens location or lens-shift and therefore will be referred to as eye/lens-shift indicator 144.

Further, the orientation misalignment indicator can include an eye orientation or tilt indicator 146 based on the determined orientation of the imaged portion of the eye, and an orientation or tilt reference 148-t. The operator of the docking system 100 can reduce the orientation misalignment or tilt of the imaged portion of the eye by aligning the eye orientation indicator 146 with the orientation or tilt reference 148-t. In embodiments where the imaged portion of the eye includes the lens 7, the eye-tilt indicator 146 can represent a lens-tilt and therefore will be referred to as eye/lens-tilt indicator 146.

FIG. 7A illustrates an embodiment where the shift reference 148-s and the tilt reference 148-t are integrated into a single target, crosshairs, or reference pattern 148 on the display unit 142. In other implementations, the references 148-s and 148-t can be separate, e.g. two target patterns displayed side-by-side, or two reference patterns displayed on separate screens, or in separate areas of the same display.

FIGS. 7A-B illustrate that the eye-shift indicator (or shift indicator) 144 and the eye-tilt indicator (or tilt indicator) 146 can be marks or icons on the display unit 142, such as the shown X and O marks. The imaging system 110 can be calibrated in such a way that the eye-shift and the eye-tilt are fully compensated or eliminated when the corresponding shift and tilt indicators 144 and 146 are manipulated to the center of the integrated reference pattern 148.

Figure 8A:
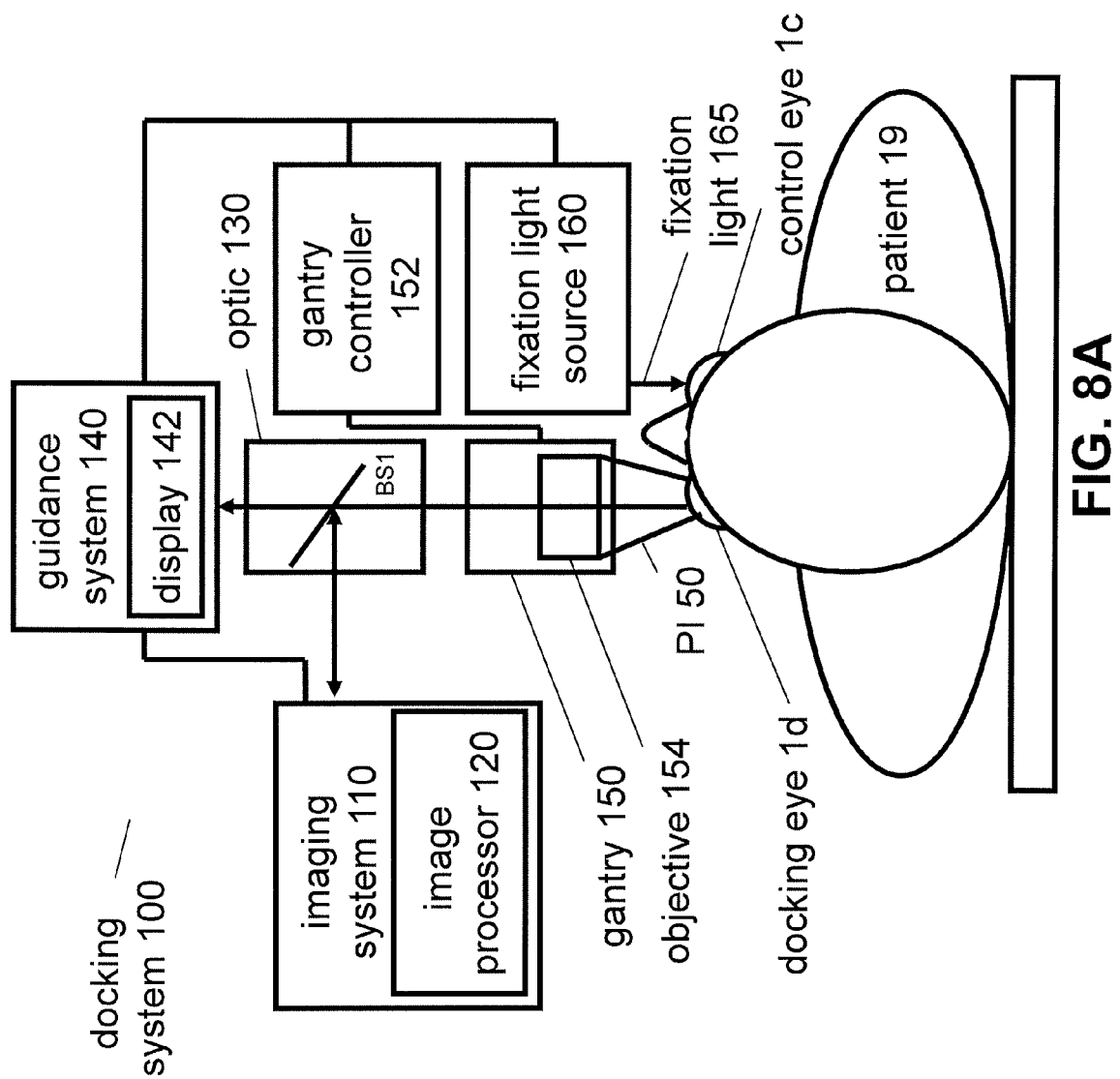
FIGS. 8A-B illustrate implementations of a guidance system with a gantry and a fixation light.

FIG. 8A illustrates that some docking systems 100 can include a gantry 150, controlled by a gantry controller 152, capable of moving essentially transverse to the PI optical axis 52 of the patient interface 50 and the optic 130. The gantry 150 may be configured to house or engage an objective 154 of the optic 130 to which the patient interface 50 may be affixed. With this design, an operator of the docking system 100 can operate the gantry 150 to move or adjust the objective 154, the patient interface 50 and its contact lens 51, thereby reducing and eventually eliminating the shift or location misalignment of the eye.

The guidance system 140 can assist the surgeon in this procedure by displaying the lens-shift indicator mark or icon 144 on the display unit 142. The surgeon can move the gantry 150 to move the shift indicator 144 closer to the center or origin of the reference 148, in essence using the reference 148 as crosshairs or a target. The shift indicator 144 reaching the center of the crosshairs 148 can signal to the surgeon that the location misalignment or shift Δ of the eye has been eliminated.

Analogously, the guidance system 140 can display the tilt indicator 146 on the display unit 142 to assist the surgeon to reduce and eventually eliminate the orientation misalignment by moving the tilt indicator 146 to the center of the reference or crosshairs 148.

The lens tilt cannot be compensated by tilting the laser system optical axis, as most laser systems or optics do not allow for such tilt. Also, moving the gantry 150 may not be able to compensate the tilt-misalignment of the lens either. Therefore, in some embodiments of the docking system 100, the surgeon may choose to instruct the patient verbally to cause the patient to rotate the imaged eye to reduce its orientation misalignment. The surgeon may monitor the movement of the tilt icon or indicator 146 when the patient rotates the eye and may give new instructions in light of the patient's actions. Giving instructions in an iterative manner may assist the surgeon to move the tilt icon 146 into the center of the crosshairs 148, reducing and eventually eliminating the tilt misalignment.

FIG. 8A illustrates that in other implementations of the docking system 100 the guidance system 140 may include a fixation light system 160, configured so that the surgeon or operator can adjust a fixation light 165 of the fixation light system 160 to guide the patient to perform at least one of a rotation or a lateral movement of the eye. The fixation light 165 can be projected into the non-docking or control eye 1c, as shown.

Figure 8B:
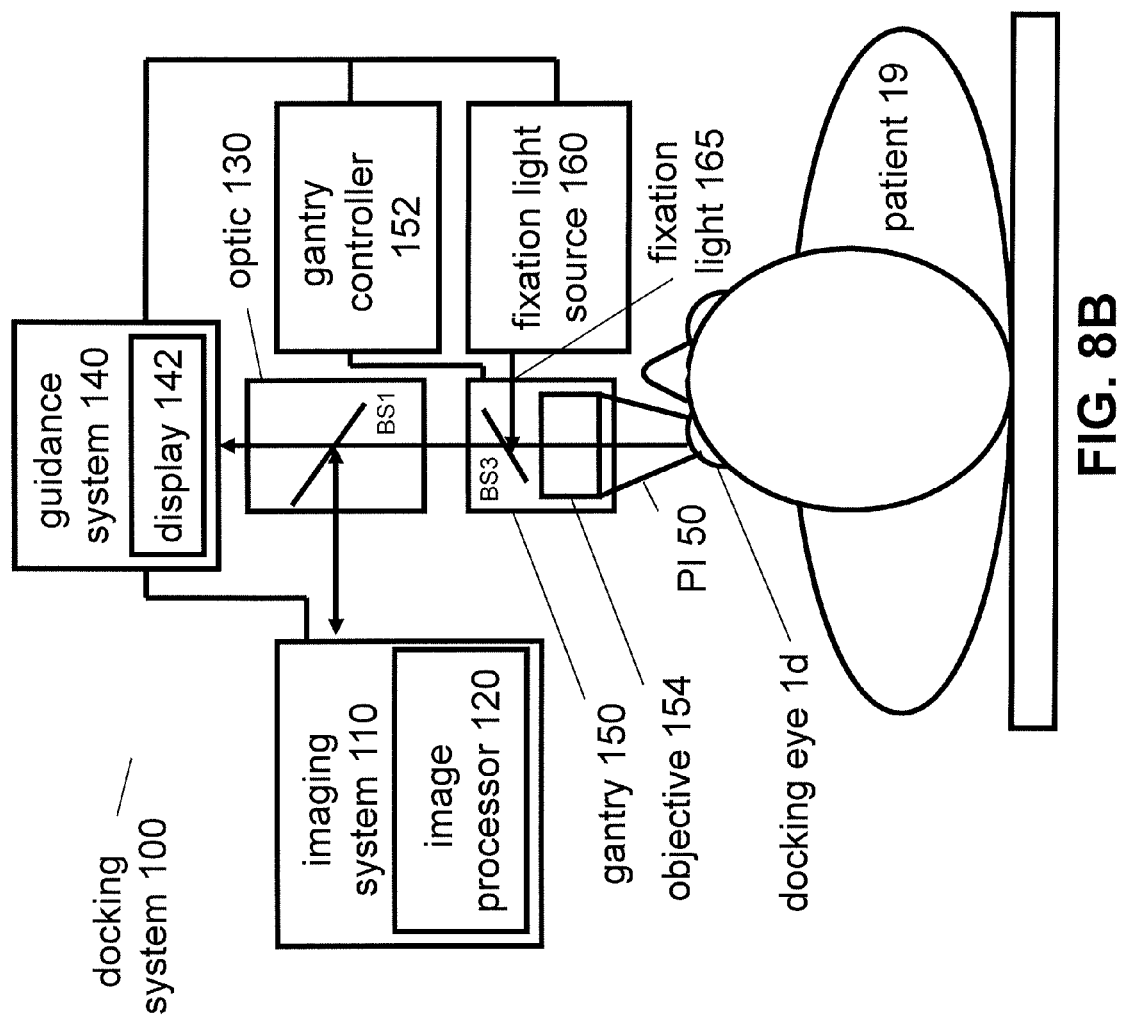

FIG. 8B illustrates that the fixation light 165 can be also projected into the docking eye 1d by an alternate embodiment of the fixation light system 160.

The fixation light system 160 can be advantageously combined with other fixation light systems, described e.g. in the jointly owned patent document "Electronically Controlled Fixation Light for Ophthalmic Imaging Systems", by T. Juhasz et al., USPTO patent application Ser. No. 12/885,193, hereby incorporated in its entirety by reference.

FIGS. 9A-C illustrate the steps of a misalignment reduction procedure. FIG. 9A illustrates the lens optical axis 11 having both a tilt φ and a shift Δ relative to the PI optical axis 52, also referred to as system optical axis 28, in a case when the lens 7 is misaligned even with the eye 1 itself.

FIG. 9B illustrates the stage of the procedure after the surgeon has caused the rotation of the patient's eye, either by giving a verbal instruction to the patient, by moving the eye 1 manually, or by adjusting the fixation light 165. At this stage the tilt misalignment φ is reduced or optimally eliminated, resulting in the lens optical axis 11 becoming aligned or parallel with the PI optical axis 52, but still having a residual shift misalignment Δ'. The reduction or elimination of the tilt misalignment φ is represented on the video display 142 by the eye/lens-tilt indicator 146 having moved to the center of the reference pattern 148, whereas the eye/lens-shift indicator 144 still being off the center of the reference pattern 148.

FIG. 9C illustrates the second stage after the surgeon has moved the gantry 150 to compensate the residual shift Δ'. At this stage the lens optical axis 11 and the PI optical axis 52 (or system optical axis 28) can be fully aligned, possibly coinciding entirely. After the residual shift Δ' is also eliminated, both the eye/lens-tilt indicator 146 and the eye/lens-shift indicator 144 are moved to the center of the reference pattern 148.

FIG. 10A illustrates that in some implementations, the docking system 100 can be configured not only to display the shift and tilt icons/indicators 144 and 146 based on the image processor 120 having processed the SB-OCT image, but also to provide an additional computed docking guidance for the surgeon. The image processor 120 can not only determine where to display the eye/lens-tilt indicator 146 and the eye/lens-shift indicator 144 relative to the reference pattern 148, but it may be configured to compute a misalignment reduction response and display it for the operator of the system as well. In particular, the image processor 120 may compute a location misalignment based on a misalignment of the determined location of the imaged portion of the eye and a location reference of the ophthalmic docking system, and display an embodiment of the location misalignment or shift indicator 144 that includes a shift correction indicator 144 based on the computed location misalignment.

In the shown implementation, the shift correction indicator 144 can be a vector, displayed on the video-monitor 142, demonstrating the direction the gantry needs to be moved to reduce the shift misalignment. A magnitude of the vector can indicate the magnitude of the gantry movement. The shift correction indicator vector 144 can be supplemented by displayed numerical correction suggestions, such as how many millimeters the gantry should be moved and in what precise direction.

FIG. 10A also illustrates an analogous tilt correction indicator 146 being part of the tilt indicator 146, computed based on a misalignment of the determined orientation of the imaged portion of the eye, such as the lens optical axis 11, and an orientation reference of the ophthalmic docking system, such as system optical axis 28 or PI optical axis 52. The guidance system 140 can display on the video-monitor or display unit 142 the orientation misalignment or tilt correction indicator 146 based on the computed orientation misalignment. The tilt correction indicator 146 can include a tilt correction vector, whose magnitude and direction, possibly supplemented with numerical values, can indicate how much should the fixation light 165 of the fixation light system 160 be moved and in which direction to compensate the tilt.

Figure 11A:
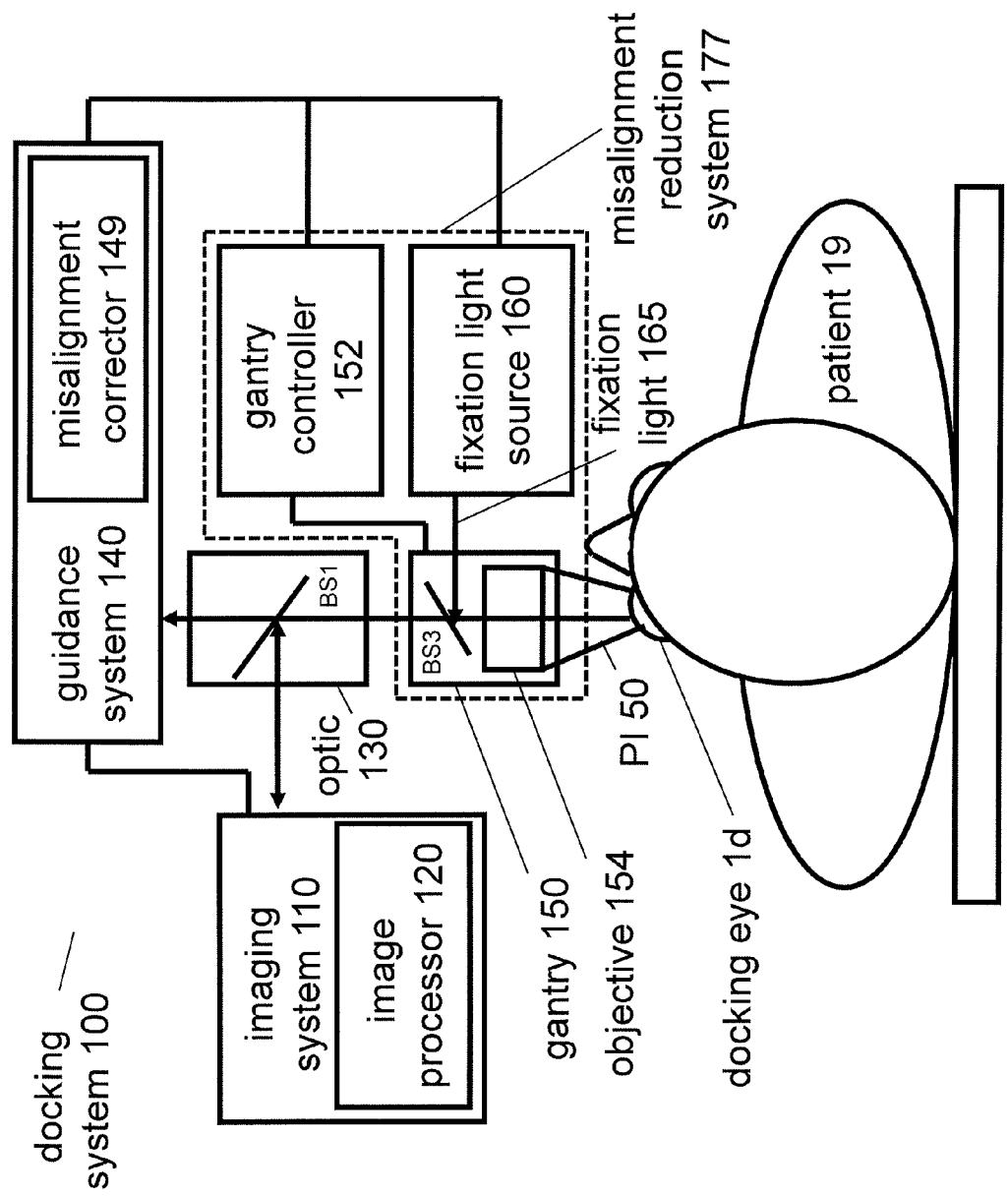
FIGS. 11A-B illustrate embodiments of the docking system.

FIG. 11A shows another embodiment of the imaging-guided docking system 100. In this docking system 100, the guidance system 140 and through it possibly the image processor 120 can be electronically coupled to a misalignment reduction system 177. The misalignment reduction system 177 may be capable of reducing one or more misalignments of the imaged eye relative to the PI optical axis 52 or in general to the optic 130.

The misalignment reduction system 177 can include the gantry 150 with the gantry controller 152, or the fixation light source 160, or both. In these implementations, the guidance system 140 may not only compute the shift and tilt correction indicators 144 and 146, as in the implementation of FIG. 10A, but may send actual control signals through the electronic coupling to at least one of the gantry controller 152 and the fixation light system 160 to actually carry out the corresponding misalignment corrections by adjusting the gantry 150 or the fixation light 165, without waiting for an analysis or intervention by the surgeon. In some implementations, the guidance system 140 may include a misalignment corrector 149 that performs the computation and the generation of the above control signals based on the image processor 120 having determined the tilt φ and a shift Δ relative to the PI optical axis 52. In other implementations, the image processor 120 itself can perform these functions.

The gantry controller 152, having received the control signal from the guidance system 140, can move the gantry 150 to adjust a position of the objective 154 to reduce the location misalignment of the imaged portion of the eye. In other examples, the fixation light system 160, having received a control signal from the guidance system 140 can generate or adjust a fixation light 165 for the eye of the patient to cause or direct a reduction of the orientation misalignment of the imaged portion of the eye. As before, the fixation light system 160 can project the fixation light 165 either into the control eye 1c or into the docking eye 1d.

In such computerized implementations, the shift and tilt misalignments may be reduced or eliminated primarily under the electronic control of the guidance system 140. These implementations may relieve the surgeon from the task of actually carrying out some or all of the compensation of the misalignment: the surgeon's duties may be lightened to only supervising the misalignment reduction performed by the computerized docking system 100.

FIG. 10B illustrates another implementation of the guidance system 140. In this example, at least one of the location misalignment indicator and the orientation misalignment indicator can include an image of a portion of a lens of the eye, indicative of the corresponding misalignment.

In the shown example, the guidance system 140 can overlay the OCT image of the lens 7 with the video-image of the eye and the reference pattern 148, constituting an integrated shift-tilt indicator 147. In some cases, the OCT image can be symbolic only, e.g. a simplified image based on a model form to the actual OCT image. The location and orientation of the overlaid lens image as the shift-tilt indicator 147 relative to the reference 148 can be an instructive display of the tilt and shift of the misalignment of the lens 7 for the surgeon. In some cases, the surgeon may be instructed to center the overlaid lens image 147 with the center of the reference 148 to eliminate the shift, and to align the major axes of the ellipsoidal lens image 147 with those of the reference pattern 148 to eliminate the tilt.

The OCT image of the lens 7, used in the shift-tilt indicator 147, can be taken e.g. the following manner. First, a circular OCT scan can be performed, resulting in a sinusoidal OCT image. The angular scan angle corresponding to the maximum and the minimum of the OCT can be identified. Then, a linear scan can be performed across the lens 7, between the maximum and minimum angle that is likely to either cross the center of the lens 7, or at least pass rather close to it. The result of this linear scan can be quite instructive about the shift and tilt of the lens 7. Thus, displaying the OCT image of the lens obtained via the linear scan on the video-microscope display 142 as the shift-tilt indicator 147 can assist the surgeon to reduce or eliminate the misalignments efficiently.

A primary function of the docking system 100 is to assist the docking of the patient interface 50 onto the eye 1. The above described embodiments that generate an image of the imaged portion of the eye before the docking and provide the shift and tilt indicators 144 and 146 in conjunction with the target reference pattern 148 carry out this function well.

The performance of the docking system 100 can be further improved by implementing an imaging system 110 that is capable of imaging the imaged portion of the eye not just before the ophthalmic docking but repeatedly during the docking.

Systems that display one or a few updated image during the docking procedure can provide valuable feedback regarding the actions of the surgeon, providing improvement in the precision and performance of the docking system 100.

Some embodiments of the imaging system 110 can offer a further qualitative improvement in this regard. They can provide not only a few updated images during docking, but an essentially live image of the docking procedure. An essentially live feedback can deliver timely information for the surgeon to center the docking with improved precision and to optimize the process in several different ways.

An often used refresh rate of live video images is typically 24 frames/second. Therefore, imaging systems that can provide images at a rate of 20-25 frames/second or higher can provide images that will appear essentially live for the surgeon. Whereas systems with a frame rate or refresh rate of less than 20-25 frames/second may not be perceived as live video imaging, but rather as jerky, jumpy images, possibly even distracting from the docking procedure.

In this respect, embodiments of the present imaging system 110 can be classified as follows. Time domain OCT, or TD-OCT systems perform an A-scan, i.e. image a range of depths corresponding to a single transverse (x,y) coordinate sequentially. Therefore, TD-OCT A-scans take a long time, and TD-OCT systems can take only several hundred to a few thousand A-scans per second. In some embodiments, their performance can be even slower. To obtain an OCT image with a reasonable resolution may require integrating several hundreds of A-scans taken along a line of (x,y) points into a B scan. Therefore, TD-OCT systems may generate B scans with a refresh rate of 1-10 frames/second, often as little as one or few frames per second. Such images appear jerky for the surgeon and provide a slower-than-live feedback for the docking process. Therefore, TD-OCT systems cannot provide feedback sufficiently fast to validate or discourage the surgeon's misalignment adjustments at the actual speed of the docking.

This slow imaging performance has disadvantages. For example, the ophthalmic docking system 100 is configured to guide and assist the alignment of the PI 50 with the eye 1 before the docking. At this pre-docked stage, the patient 19 is still capable of moving the eye 1. In particular, the patient is breathing, moving the eye up and down. At low imaging speeds, a TD-OCT imaging system cannot keep up with the up-and-down breathing motion of the eye, causing the TD-OCT imaging system to display motional artifacts, such as jumps in the image and discontinuous image lines.

In contrast, Spectrometer-Based, or SB-OCT systems gather image data at an (x,y) point from all depths simultaneously. These images are sometimes still called A-scans, even though no sequential scanning is involved. Because of the parallel or simultaneous nature of gathering the image-data from different depths, SB-OCT systems can take up to 500,000 A-scans per second. Therefore, the same B-scan containing several hundred A-scans as above, can be generated with a refresh rate of higher than 20 frames per second, possibly up to 1,000 frames per second.

It is noted here that actually displaying these images also takes time and can be limited by the electronic performance of the OCT display unit 142. The above cited refresh rates characterize the speed of image-acquisition by the imaging system 110. The speed of display can be slower, depending on the electronic and data-transfer limiting factors.

The performance of SB-OCT systems can be further accelerated by using dedicated processors and pre-computed scanning patterns stored in dedicated memories to drive the scanning of the imaging beam fast, as described e.g. in the above-referenced US Patent Application "Image-Guided Docking for Ophthalmic Surgical Systems" by A. Juhasz and K. Vardin.

Given that the imaging speeds of the SB-OCT and TD-OCT imaging systems are on opposite sides of the live video-rate of 20-25 frames/second, embodiments of the imaging system 110 that use SB-OCT imaging systems are capable of providing timely and smooth live feedback information for the surgeon free of motional artifacts, whereas typical TD-OCT imaging systems are not capable of providing smooth live feedback for the surgeon and are prone to display motional artifacts. Systems with live imaging feedback, as discussed above, offer qualitatively improved precision of the docking procedure.

Further, the superior imaging speed allows SB-OCT imaging systems 110 to create much more complex, sharp and detail-rich images and still provide the images as a live video. Examples include two dimensional images of the lens 7 or scanning the lens 7 along several circles to map out the actual shape of the lens 7 instead of using models and relying on assumptions about the geometry and shape of the lens 7.

A final factor, impacting the long term performance of embodiments of the imaging system 110 is that SB-OCT systems do not have moving parts and thus their reliability and serviceability is quite satisfactory. In contrast, TD-OCT systems have rapidly moving parts, associated with the movement of a reference mirror in a reference arm of the OCT apparatus. Obviously, the presence of moving parts in the TD-OCT systems increases the chance of malfunction and misalignment, thus possibly decreasing their overall performance, demanding more frequent field-service and still facing the possibility of long-term performance degradation.

In sum, TD-OCT systems are not necessarily equivalent to SB-OCT systems, at least for the following reasons. (i) TD-OCT systems do not provide live imaging, or feedback images at refresh rates useful for high precision docking and surgical processes. (ii) TD-OCT systems are prone to display motional artifacts. (iii) TD-OCT systems may also have difficulties providing 2D scanning images or high precision, detail-rich images. (iv) Finally, TD-OCT imaging systems require field services and maintenance much more often than SB-OCT system. Thus, TD-OCT systems and SB-OCT systems are sufficiently different so that for many applications they are not equivalent embodiments of a generic OCT system. Rather, the degree of difference between their performances for the specific application is to be analyzed on a case-by-case basis.

Figure 11B:
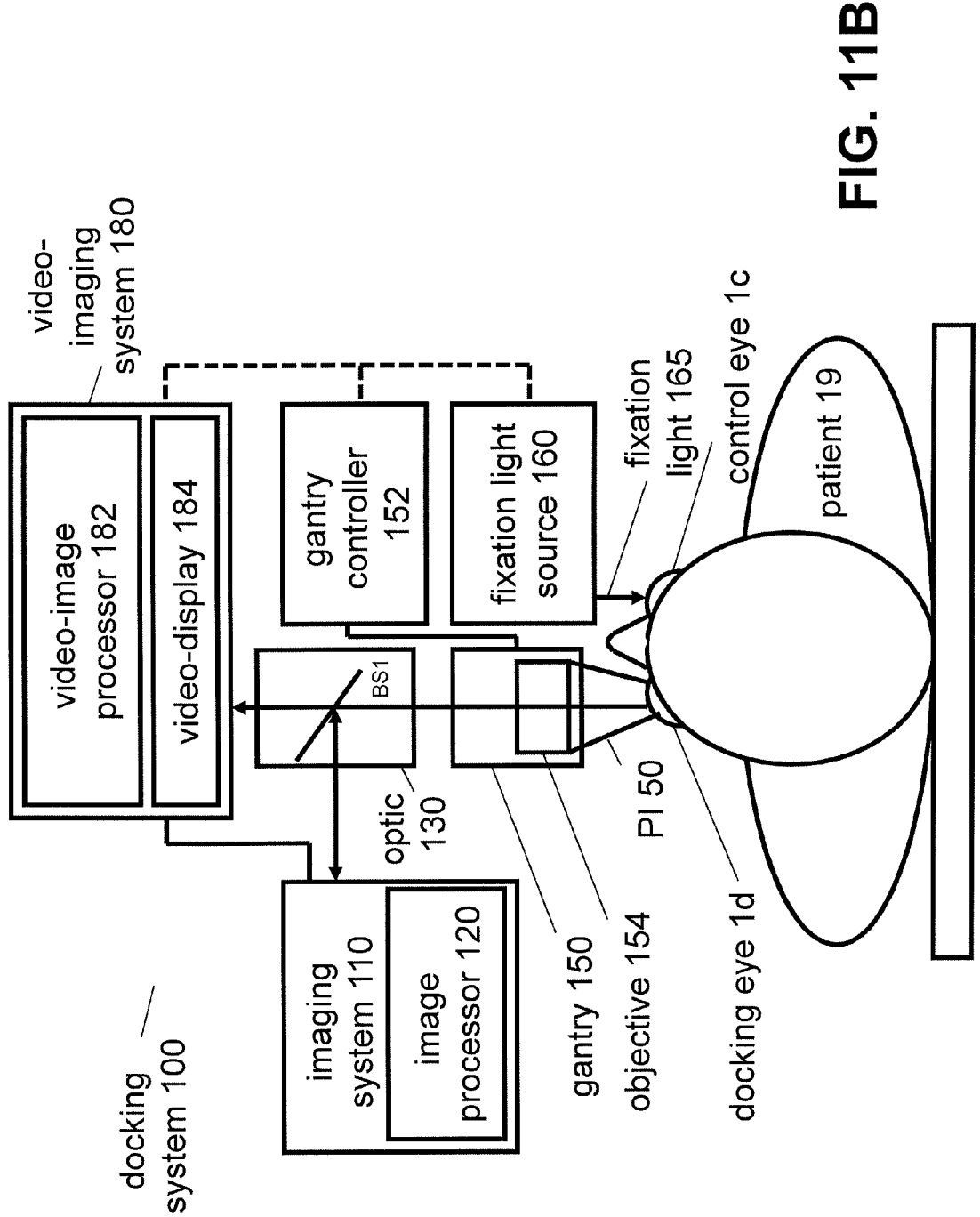

FIG. 11B illustrates that other implementations of the docking system 100 may acquire some of the misalignment information from a video image created by a video-imaging system 180. In these docking systems 100, embodiments of the ophthalmic imaging system 110 can include an OCT or an in-depth imaging system 110 that can generate an in-depth image of an internal eye-structure of the eye 1. The image processor 120 can include an in-depth image processor 120 that can determine an orientation of the internal eye-structure from the in-depth image of the internal eye-structure.

In addition, the docking system 100 and in particular the guidance system 140 can include the video-imaging system 180 that can include a video-image processor 182 and a video-display 184 that can be analogous to the video microscope display 142. The video-imaging system 180 can be configured to video-image a frontal eye-structure of the eye, and the video-image processor 182 can be configured to determine a location of the frontal eye-structure from the video-image of the frontal eye-structure. As before, the video-imaging system 180 can be coupled to the ophthalmic imaging system 110 and can be configured to display on the video-display 184 an orientation misalignment indicator using the determined orientation of the internal eye-structure, determined by the image processor 120, and a location misalignment indicator using the determined location of the frontal eye-structure, determined by the video-image processor 182.

In some implementations, the in-depth image processor 120 can perform an image recognition process to recognize a portion of the ACL scan-image 114 and a portion of the PCL scan-image 116 in the image of the internal eye-structure, which can be the lens 7, or its capsular bag or its hardened nucleus.

The in-depth image processor 120 can determine the orientation or tilt misalignment of the imaged internal eye-structure based on the results of the image recognition process by performing any of the methods described in relation to FIG. 6 and subsequently, involving phases and amplitudes of the scan-image.

The video-image processor 182 can perform a video-image recognition process to recognize an image of the frontal eye-structure in the video-image, and to determine a location of the frontal eye-structure based on the result of the video-image recognition process. The imaged frontal eye-structure can be the pupil 6 or the limbus 5 of the eye, for example.

As it has been described in relation to FIGS. 4-6, the analysis by the in-depth image processor 120 can determine not only the orientation of the lens 7, the internal eye-structure, but also its location. Therefore, in some implementations, the docking system 100 could determine two locations: the location of the imaged internal eye-structure as determined by the in-depth image processor 120, and the location of the frontal eye-structure as determined by the video-imaging system 180. Since the internal eye structure may not be fully aligned with the eye, these two locations may be different.

Aligning the patient interface 50 with the location of the imaged internal eye-structure, with the location of the frontal eye-structure, or with an intermediate or averaged location generated using both of these locations may be advantageous for various purposes.

FIGS. 7A-B and FIG. 10A illustrate that after the image recognition steps were performed by the in-depth imaging system 110 and the video-imaging system 180, the video-display 184 can display an eye-orientation misalignment indicator related to the determined orientation of the imaged internal eye-structure that includes the eye-orientation indicator 146 and the orientation reference 148. In the embodiment where the imaged internal eye-structure is the lens 7, the surgeon can reduce the lens-tilt misalignment by aligning the lens-tilt indicator 146 with the orientation reference 148. As described in relation to FIGS. 7-10, the surgeon can achieve this alignment by instructing the patient 19 to rotate the docking eye, or by manually rotating the eye 1, or by adjusting the fixation light source 160, among others.

The video-display 184 can also display a location misalignment indicator that includes the eye-location indicator 144 related to the determined location of the video-imaged frontal eye-structure, and the location reference 148 of the ophthalmic docking system. As before, the operator of the ophthalmic docking system 100 can reduce a lens location misalignment by aligning the lens location indicator 144 with the location reference 148. As described in relation to FIGS. 7-10, the surgeon can reduce this location misalignment by operating the gantry 150.

The docking system 100 of FIG. 11B can be used in combination with any block or unit of the previously described embodiments of FIG. 2, FIGS. 8A-B and FIG. 11A. For example, the docking system 100 can include the fixation light source 160, configured to adjust the fixation light 165 in relation to at least one of the location misalignment indicator and the orientation misalignment indicator.

Figure 12:
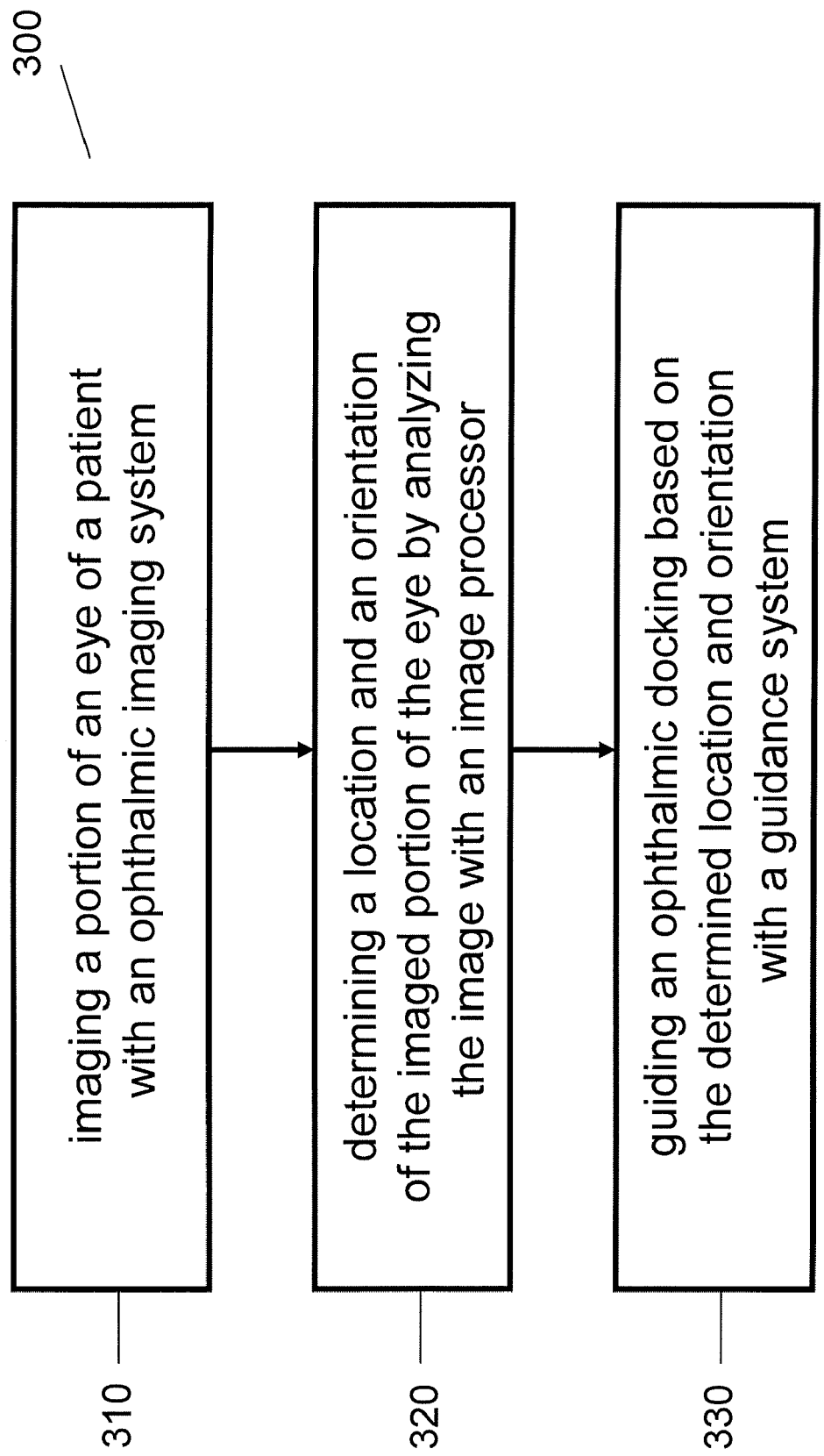
FIG. 12 illustrates a method of operating the imaging-guided docking system.

FIG. 12 illustrates that an embodiment of a method 300 of guiding an ophthalmic docking can include: an imaging 310 of a portion of the eye 1 of the patient 19 with the ophthalmic imaging system 110; a determining 320 of a location and an orientation of the imaged portion of the eye 1 by analyzing the image with the image processor 120; and a guiding 330 of an ophthalmic docking based on the determined location and orientation with the guidance system 140.

The imaging 310 can include imaging at least one of a lens-capsule, the anterior capsular layer ACL 14, the posterior capsular layer PCL 16, a lens target region, the lens 7, its nucleus, the cornea 2, the iris 3, the limbus 5, the pupil 6, a corneal endothelium and a corneal epithelium.

In embodiments where the imaging 310 includes imaging a portion of the lens 7 of the eye, the determining 320 can include performing an image recognition process to recognize an ACL scan-image 114 of the anterior capsular layer ACL 14 and to recognize a PCL scan-image 116 of the posterior capsular layer PCL 16 in the image.

As described in relation to FIG. 6, once the image recognition has been performed, the determining 320 can further include determining an anterior phase and an anterior amplitude of the ACL scan-image 114 and a posterior phase and a posterior amplitude of the PCL scan-image 116, and determining the location and the orientation of the lens 7 from the anterior phase, the anterior amplitude, the posterior phase and the posterior amplitude.

In other embodiments, the determining 320 can include determining an anterior maximum depth and an anterior minimum depth of the anterior capsular layer and a posterior maximum depth and a posterior minimum depth of the posterior capsular layer along a scanning variable; and determining the location and the orientation of the lens 7 from the anterior maximum depth, the anterior minimum depth, the posterior maximum depth, and posterior minimum depth.

In yet other embodiments, the determining 320 can include recognizing an image of a capsular layer portion of the lens in the image; determining a phase and an amplitude of the capsular layer; and determining a location and an orientation of the lens using the determined phase and amplitude.

The guiding 330 can include displaying a location misalignment indicator based on the determined location of the imaged portion of the eye, and displaying an orientation misalignment indicator based on the determined orientation of the imaged portion of the eye.

The guiding 330 can also include displaying, as part of the location misalignment indicator, the eye or lens location indicator 144 based on the determined location of the imaged portion of the eye and the location reference 148-s of the ophthalmic docking system, and displaying as part of the orientation misalignment indicator, the eye or lens orientation indicator 146 based on the determined orientation of the imaged portion of the eye and the orientation reference 148-t of the ophthalmic docking system. The orientation reference 148-t and the location reference 148-s can be the same target or reference pattern 148.

The guiding 330 can also include displaying the location misalignment indicator to assist an operator of the ophthalmic docking system 100 to operate the gantry 150 to reduce an eye or lens location misalignment. Further, the guiding 330 can also include displaying the orientation misalignment indicator 146 to assist the surgeon to instruct the patient 19 to rotate the eye, or to manually rotate the eye, or to adjust the fixation light source 160 to reduce an eye orientation misalignment.

The method 300 can include performing repeatedly the imaging 310, the determining 320, and the guiding 330. The guiding 330 may include updating the display of the location misalignment indicator and the orientation misalignment indicator according to the repeated imaging 310 and determining 320 during the ophthalmic docking. Such a repeat performance of the guiding method 300 can provide valuable feedback for the surgeon, improving the precision of the docking process. A further qualitative improvement can be achieved by updating the image or repeating the imaging at a live video refresh rate, such as at 20-25 frames/second or faster. Repeating the method 300 at such video rates may be able to provide a live video feedback for the surgeon.

Figure 13:
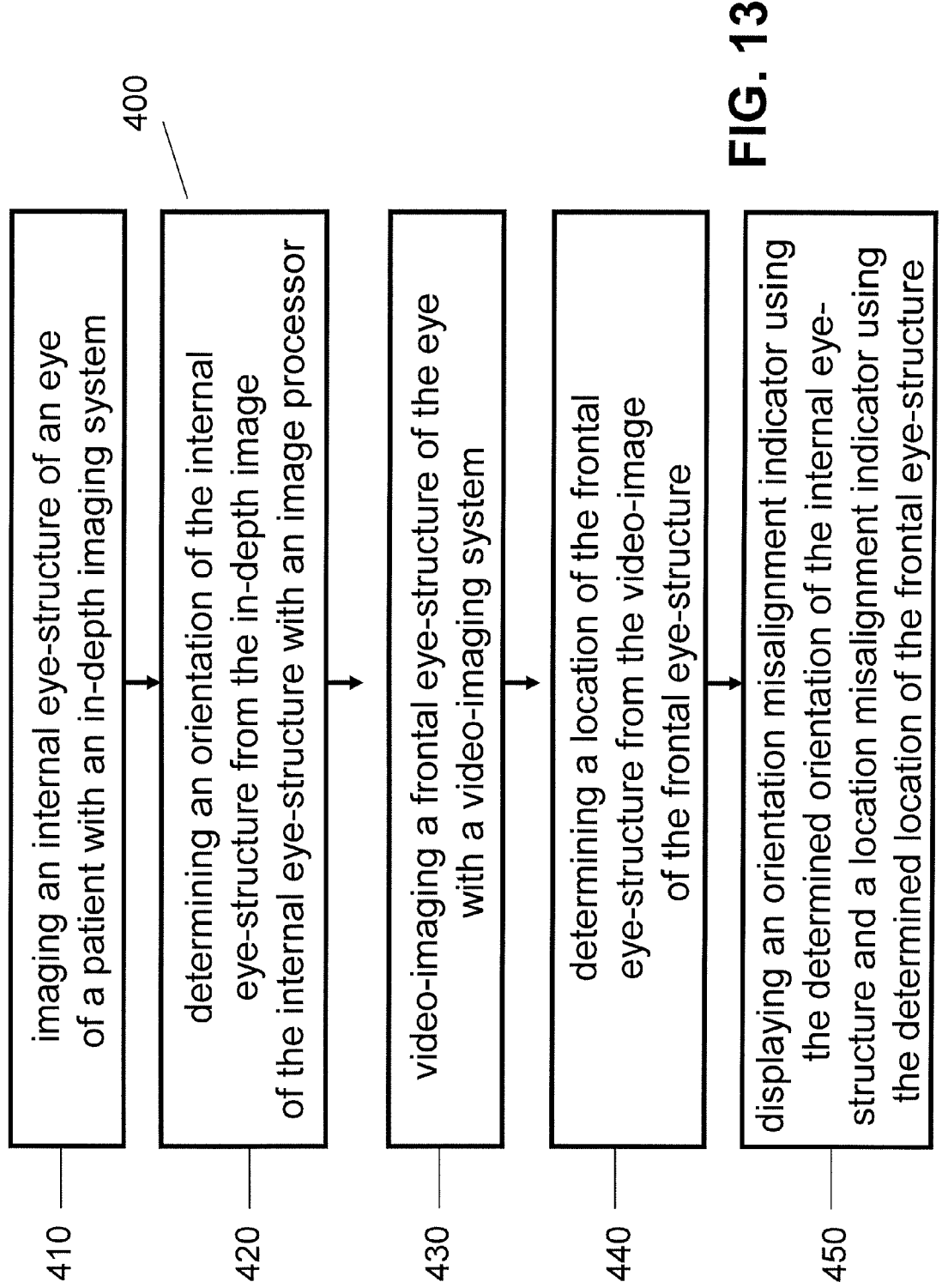
FIG. 13 illustrates another method of operating the imaging-guided docking system.

FIG. 13 illustrates that an alternative method 400 of guiding an ophthalmic docking can include: an imaging 410 of an internal eye-structure of an eye of a patient with the in-depth imaging system 110; a determining an orientation 420 of the internal eye-structure from the in-depth image of the internal eye-structure with the image processor 120; a video-imaging 430 of a frontal eye-structure of the eye with the video-imaging system 180; a determining of a location 440 of the frontal eye-structure from the video-image of the frontal eye-structure with the video-image processor 182; and a displaying 450 of an orientation misalignment indicator using the determined orientation of the internal eye-structure and a location misalignment indicator using the determined location of the frontal eye-structure with the guidance system 140 or the video display unit 184.

Another embodiment of the alignment guidance system 140 can include a system that provides guidance for the precise attachment of the patient interface 50 onto a distal tip of the ophthalmic docking system 100, its optic 130 or its objective 154. The precision of the corneal flaps, created during LASIK procedures, is very sensitive to even the smallest misalignments of the PI optical axis 52 with the system optical axis 28, even of the order of ten microns. Therefore, considerable performance improvements can be achieved by applying the imaging-based guidance system 140 to image the patient interface 50 itself before and during the process of attaching it to the distal end of the system 100 even before any docking process is initiated, and to provide a guidance to the surgeon to adjust the PI 50 based on the imaged misalignments of the PT 50 and the objective 154.

Yet another application can be to use the guidance system 140 not to assist a docking procedure, but in conjunction with an ultrasound-based phaco surgical system to guide the precise targeting of the various surgical steps, including the insertion of the phaco-tip by the ophthalmic surgeon.

In yet another implementation, the ophthalmic guidance system 140 may be coupled to the ophthalmic imaging system 110 that includes a Spectrometer Based OCT (SB-OCT) imaging system. The imaging system 110 can be configured to generate a live image of an ophthalmic region modified by a surgical procedure. In some implementations, the image-refresh rate can be 20-25 frames/second or greater.

In the above specification, numerous systems included one or more programmable processors, and numerous method steps included the processors functioning based on a corresponding stored program. In these systems, embodiments exist in which the systems include memory systems, associated with the processors that are capable of storing the corresponding programs, and program means that are stored in the memory systems. For example, the image processor 120, the guidance system 140, the gantry controller 152, the misalignment reduction system 177, and the video-image processor 182 all have embodiments that include a memory or memory systems corresponding to these processors that are capable of storing a program or program means for their processor, possibly on computer-readable media.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

What is claimed is:

1. An ophthalmic docking system, comprising:
an ophthalmic imaging system, comprising
an optical coherence tomographic imaging system, configured to image a portion of an eye of a patient during a docking of a patient interface to the eye, and
an image processor configured to determine a location and an orientation of the imaged portion of the eye by analyzing the image; and
a guidance system, coupled to the ophthalmic imaging system, configured to guide the docking based on the determined location and orientation before the patient interface is docked to the eye, wherein: the imaged portion of the eye comprises an imaged portion of a lens of the eye; and the image processor is configured to perform an image recognition process to recognize a scan-image of an anterior capsular layer of the lens and a scan-image of a posterior capsular layer of the lens in the image; and wherein: the image processor is configured to determine an anterior maximum depth and an anterior minimum depth of the anterior capsular layer and a posterior maximum depth and a posterior minimum depth of the posterior capsular layer along a scanning variable, and to determine the location and the orientation of the lens from the anterior maximum depth, the anterior minimum depth, the posterior maximum depth, and posterior minimum depth.

2. The ophthalmic docking system of claim 1, the optical coherence tomographic imaging system comprising:
at least one of a time domain optical coherence tomography (OCT) system, a frequency domain OCT system, and a spectrometer-based OCT system.

3. The ophthalmic docking system of claim 1, the optical coherence tomographic imaging system comprising:
a scanning imaging system, configured
to perform a scan by directing an imaging beam to points of at least one of an arc, a line, a loop, a circle, an ellipse, a star, a line with repeated features, a two dimensional pattern and a two dimensional mesh, and
to image the imaged portion of the eye in a depth-range at points of the scan.

4. The ophthalmic docking system of claim 1,
the imaged portion of the eye comprises at least one of a lens-capsule, an anterior lens capsular layer, a posterior lens capsular layer, a lens target region, a lens, and a nucleus.

5. The ophthalmic docking system of claim 1, wherein:
the image processor is configured to analyze the scan-images of the recognized layers by using a geometric model of the lens to determine a location and an orientation of the lens.

6. The ophthalmic docking system of claim 1, wherein:
the image processor is configured
to determine an anterior phase and an anterior amplitude of the scan-image of the anterior capsular layer and a posterior phase and a posterior amplitude of the scan-image of the posterior capsular layer, and
to determine the location and the orientation of the lens from the anterior phase, the anterior amplitude, the posterior phase and the posterior amplitude.

7. The ophthalmic docking system of claim 1, wherein:
the guidance system comprises a display unit; and
the guidance system is configured to display on the display unit
a location misalignment indicator based on the determined location of the imaged portion of the eye, and
an orientation misalignment indicator based on the determined orientation of the imaged portion of the eye.

8. The ophthalmic docking system of claim 7, wherein:
the location misalignment indicator comprises
an eye location indicator based on the determined location of the imaged portion of the eye, and
a location reference of the ophthalmic docking system, wherein
an operator of the ophthalmic docking system can reduce an eye location misalignment by aligning the eye location indicator and the location reference; and
the orientation misalignment indicator comprises
an eye orientation indicator based on the determined orientation of the imaged portion of the eye, and
an orientation reference of the ophthalmic docking system, wherein
the operator of the ophthalmic docking system can reduce an eye orientation misalignment by aligning the eye orientation indicator and the orientation reference.

9. The ophthalmic docking system of claim 7, wherein:
the ophthalmic guidance system is configured
to display the location misalignment indicator to assist an operator of the ophthalmic docking system to operate a gantry of the ophthalmic docking system to reduce an eye location misalignment, and
to display the orientation misalignment indicator to assist the operator of the ophthalmic docking system to cause the patient to rotate the eye to reduce an eye orientation misalignment.

10. The ophthalmic docking system of claim 9, wherein:
the guidance system comprises a fixation light system, configured so that the operator can adjust a fixation light of the fixation light system to guide the patient to perform at least one of a rotation of the eye and a lateral movement of the eye.

11. The ophthalmic docking system of claim 7, wherein:
at least one of the location misalignment indicator and the orientation misalignment indicator comprises an image of a portion of a lens of the eye, indicative of the corresponding misalignment.

12. The ophthalmic docking system of claim 1, wherein:
the ophthalmic imaging system is configured to image the imaged portion of the eye repeatedly during the ophthalmic docking.

13. The ophthalmic docking system of claim 12, wherein:
the ophthalmic imaging system comprises a spectrometer based OCT imaging system, configured to image the imaged portion of the eye with a refresh rate of at least 20 frames/second.

14. The ophthalmic docking system of claim 1, the ophthalmic imaging system comprising:
a video-imaging system configured to generate a video-image of a frontal eye-structure of the eye, wherein
the imaged portion of the eye comprises the internal eye-structure and the frontal eye-structure.

15. The ophthalmic docking system of claim 14, the image processor comprising:
an in-depth image processor, configured to determine an orientation of an internal eye-structure from the image of the internal eye-structure, generated by the optical coherence tomographic imaging system; and
a video-image processor configured to determine a location of the frontal eye structure from the video-image of the frontal eye-structure.

16. The ophthalmic docking system of claim 15, wherein:
the in-depth image processor is configured
to perform an image recognition process to recognize an image of a portion of an anterior capsular layer of a lens of the eye, and an image of a portion of a posterior capsular layer of the lens of the eye in the in-depth image of the internal eye-structure, and
to determine the orientation of the internal eye-structure based on a result of the image recognition process.

17. The ophthalmic docking system of claim 15, wherein:
the video-image processor is configured
to perform a video-image recognition process to recognize an image of the frontal eye-structure in the video-image, and
to determine the location of the frontal eye-structure based on a result of the video-image recognition process.

18. The ophthalmic docking system of claim 15, wherein:
the in-depth image processor is configured to determine a location of the imaged internal eye-structure; and
the ophthalmic docking system is configured to determine the location of the imaged portion of the eye using the determined location of the internal eye-structure and the determined location of the frontal eye-structure.

19. The ophthalmic docking system of claim 14, the guidance system comprising:
a video-display unit, configured to display
an orientation misalignment indicator related to the orientation of the internal eye-structure, and
a location misalignment indicator related to the location of the frontal eye-structure.

20. A method of guiding an ophthalmic docking, the method comprising:
imaging a portion of an eye of a patient during a docking of a patient interface to the eye with an optical coherence tomographic imaging system of an ophthalmic imaging system;
determining a location and an orientation of the imaged portion of the eye by analyzing the image with an image processor; and
guiding the docking based on the determined location and orientation with a guidance system before the patient interface is docked to the eye wherein: the imaging comprises imaging a portion of a lens of the eye; and the determining comprises performing an image recognition process to recognize a scan-image of an anterior capsular layer and a scan-image of a posterior capsular layer in the image by the image processor; and the determining comprising: determining an anterior phase and an anterior amplitude of the scan-image of the anterior capsular layer and a posterior phase and a posterior amplitude of the scan-image of the posterior capsular layer; and determining the location and the orientation of the lens from the anterior phase, the anterior amplitude, the posterior phase and the posterior amplitude.

21. The method of claim 20, the imaging comprising:
imaging at least one of a lens-capsule, an anterior capsular layer, a posterior capsular layer, a lens target region, a lens, and a nucleus.

22. The method of claim 20, the guiding comprising:
displaying a location misalignment indicator based on the determined location of the imaged portion of the eye; and
displaying an orientation misalignment indicator based on the determined orientation of the imaged portion of the eye.

23. The method of claim 20, the guiding comprising:
displaying the location misalignment indicator to assist an operator of the ophthalmic docking system to operate a gantry of the ophthalmic docking system to reduce an eye location misalignment; and
displaying the orientation misalignment indicator to assist the operator of the ophthalmic docking system to cause the patient to rotate the eye to reduce an eye orientation misalignment.

24. The method of claim 20, the imaging comprising:
imaging an internal eye-structure of an eye of the patient with an optical coherence tomographic imaging system; and
video-imaging a frontal eye-structure of the eye with a video-imaging system, wherein
the imaged portion of the eye comprises the internal eye-structure and the frontal eye-structure.

25. The method of claim 24, the determining comprising:
determining an orientation of the internal eye-structure from the image of the internal eye-structure with an in-depth image processor; and
determining a location of the frontal eye structure from the image of the frontal eye-structure with a video-image processor.

26. The method of claim 20, the guiding comprising:
displaying on a video-display unit
an orientation misalignment indicator related to the orientation of the internal eye-structure, and
a location misalignment indicator related to the location of the frontal eye-structure.

27. The method of claim 26, the method comprising:
performing repeatedly the imaging the portion of the eye, the determining the location and the orientation of the imaged portion of the eye, the displaying the location misalignment indicator, and the displaying the orientation misalignment indicator during the ophthalmic docking.

28. An ophthalmic docking system, comprising:
an ophthalmic imaging system, comprising
an optical coherence tomographic imaging system configured to image a portion of an eye of a patient during a docking of a patient interface to the eye, and
an image processor configured
to process the image to recognize an ophthalmic structure of the eye, and
to determine a misalignment of the imaged portion of the eye relative to a reference; and
a guidance system, coupled to the ophthalmic imaging system, configured to guide the docking based on the determined misalignment before the patient interface is docked to the eye wherein: the imaged portion of the eye comprises an imaged portion of a lens of the eye; and the image processor is configured to perform an image recognition process to recognize a scan-image of an anterior capsular layer of the lens and a scan-image of a posterior capsular layer of the lens in the image, and wherein: the image processor is configured to determine an anterior phase and an anterior amplitude of the scan-image of the anterior capsular layer and a posterior phase and a posterior amplitude of the scan-image of the posterior capsular layer, and to determine the location and the orientation of the lens from the anterior phase, the anterior amplitude, the posterior phase and the posterior amplitude.

29. The ophthalmic docking system of claim 28, the misalignment comprising:
a location misalignment and an orientation misalignment.

30. The ophthalmic docking system of claim 28, wherein:
the image processor is configured to compute a misalignment-reducing compensation.

31. The ophthalmic docking system of claim 30, wherein:
the ophthalmic docking system is configured to perform a misalignment-reducing response based on the misalignment-reducing compensation.

32. The ophthalmic docking system of claim 31, wherein:
the ophthalmic docking system comprises a gantry; and
the misalignment-reducing response comprises the gantry being operated to reduce a location misalignment.

33. The ophthalmic docking system of claim 31, wherein:
the ophthalmic docking system comprises a fixation light system; and
the misalignment-reducing response comprises the fixation light system being operated to reduce an orientation misalignment.

\* \* \* \* \*